(12) United States Patent
Econs et al.

(10) Patent No.: US 7,947,810 B2
(45) Date of Patent: *May 24, 2011

(54) KITS FOR DIAGNOSING A HYPOPHOSPHATEMIC DISORDER

(75) Inventors: Michael Econs, Indianapolis, IN (US); Ken White, Carmel, IN (US); Tim Matthias Strom, Munich (DE); Thomas Meitinger, Munich (DE)

(73) Assignees: Advanced Research & Technology Institute, Indianapolis, IN (US); Ludwig-Maximilians-Universitat Munchen Abeteilung Mediziniche Genetik, Munich (DE)

( * ) Notice: Subject to any disclaimer, the term of this patent is extended or adjusted under 35 U.S.C. 154(b) by 129 days.

This patent is subject to a terminal disclaimer.

(21) Appl. No.: 11/983,190

(22) Filed: Nov. 7, 2007

(65) Prior Publication Data
US 2009/0311792 A1 Dec. 17, 2009

Related U.S. Application Data

(62) Division of application No. 10/379,334, filed on Mar. 4, 2003, now Pat. No. 7,314,618, which is a division of application No. 09/901,938, filed on Jul. 10, 2001, now Pat. No. 7,223,563.

(60) Provisional application No. 60/219,137, filed on Jul. 19, 2000.

(51) Int. Cl.
*C07K 16/22* (2006.01)
(52) U.S. Cl. .................................................. 530/387.9
(58) Field of Classification Search ........................ None
See application file for complete search history.

(56) References Cited

U.S. PATENT DOCUMENTS
2002/0082205 A1* 6/2002 Itoh et al. ..................... 514/12

FOREIGN PATENT DOCUMENTS

| WO | WO 00/73454 | 12/2000 |
|---|---|---|
| WO | WO 01/40466 | 6/2001 |
| WO | WO 01/42451 | 6/2001 |
| WO | WO 01/49740 | 7/2001 |
| WO | WO 01/60850 | 8/2001 |
| WO | WO 01/61007 | 8/2001 |
| WO | WO 01/66595 | 9/2001 |

OTHER PUBLICATIONS

Bainchine, et al., 1971, Birth Defects Orig. Aric. Ser., 7:287-295.
Bonaventure, et al., 1994, Exp. Cell Res., 212:97-104.
Carthew, 2001, Curr. Opin. Cell Biol., 13:244-248.
Cranage, et al., 1986, EMBO J., 5:3057-3063.
Econs, et al., 1997, J. Clin. Endocrinol. Metab. 82:674-681.
Econs, et al., 1994, Bone and Min., 24:17-24.
Elbashir, et al., 2001, Nature, 411:494-498.
Haselhoff, et al., 1988, Nature, 334:585-591.
Kay, et al., 1997, Proc. Natl. Acad. Sci. U.S.A., 94:12744-12746.
Nagy and Rossant (1993, In: Gene Targeting, A Practical Approach, pp. 146-179, Joyner ed., IRL Press).
Rowe, et al., 1991, Hum. Genet., 89:539-542.
Tanner, et al., In: Antisense Research and Applications, CRC Press Inc., 1993, pp. 415-426.
Econs, et al., "Autosomal dominant hypophosphatemic rickets is linked to chromosome 12p13." 1997, J Clin Invest 100(11):2653-2657.
Lorenz-Depiereux et al., The autosomal dominant hypophosphatemic rickets (ADHR) gene is a secreted fibroblast growth factor (FGF23) 2001, European Journal of Human Genetics 9(suppl 1):P0772.
Turner, et al., "Review post-transcriptional gene-silencing and RNA interference: genetic immunity, mechanisms and applications." 2000, J Chem. Technol Biotechnol 75:869-882.
White, et al., "The naturally occurring autosomal dominant hypophosphatemic rickets (ADHR) mutations stabilize full-length FGF-23" 2001, Journal of Bone and Mineral Research 16(Suppl 1):S152.

* cited by examiner

*Primary Examiner* — Christine J Saoud
(74) *Attorney, Agent, or Firm* — Riverside Law LLP

(57) ABSTRACT

The present invention relates to a kit for diagnosing a disorder comprising a reagent that detects FGF23 polypeptides and mutant FGF23 polypeptides.

1 Claim, 19 Drawing Sheets

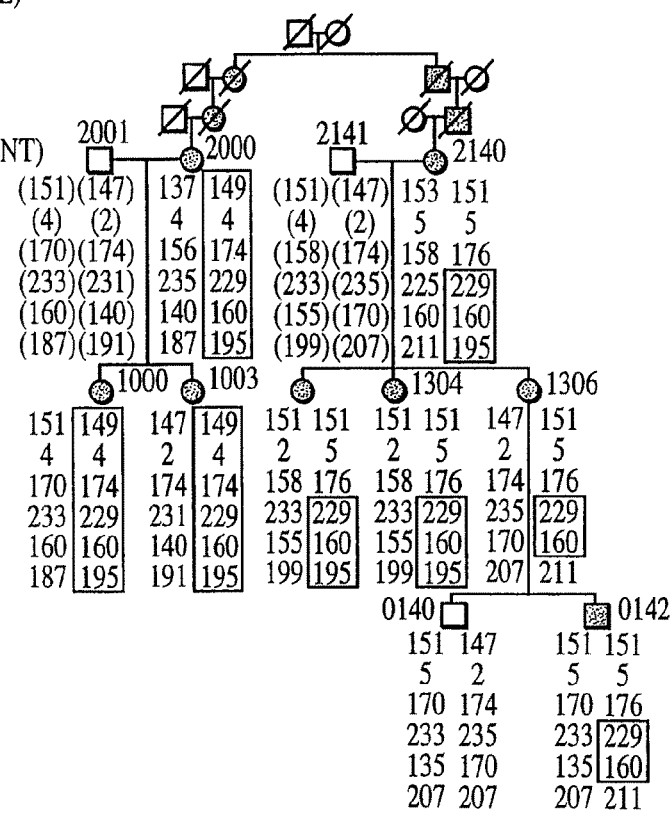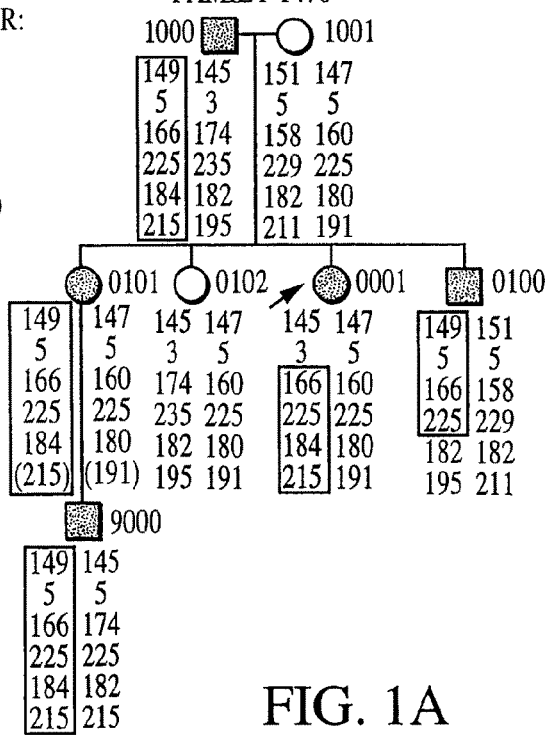
FIG. 1A

FIG. 3A

```
FGF12  VVAIQGVKASLYVAMNGEGYLYSSDV.FTPECKFKESVFENYYVIYSSTLY...  164
FGF14  VVAIQGVKTGLYIAMNGEGYLYPSEL.FTPECKFKESVFENYYVIYSSMLY...  162
FGF13  VVAIQGVQTKLYLAMNSEGYLYTSEL.FTPECKFKESVFENYYVTYSSMIY...  160
FGF11  VVTIQSAKLGHYMAMNAEGLLYSSPH.FTAECRFKECVFENYVLYASALY...  162
FGF16  LISIRGVDSGLYLGMNERGELYGSKK.LTRECVFREQFEENWYNTYASTLY...  152
FGF9   LVSIRGVDSGLYLGMNEKGELYGSEK.LTQECVFREQFEENWYNTYSSNLY...  153
FGF10  VVAVKAINSNYYLAMNKKGKLYGSKE.FNNDCKLKERIEENGYNTYASFNW...  169
FGF7   IVAIKGVEFYLAMNKEGKLYAKKE.CNEDCNFKELILENHYNTYASAKW...  156
FGF3   IVAIRGLFSGRYLAMNKRGRLYASEH.YSAECEFVERIHELGYNTYASRLYRTV  137
FGF1   EVYIKSTETGQYLAMDTDGLLYGSQT.PNEECLFLERLESNNHYNTYISKKH...  117
FGF2   VVSIKGVCANRYLAMKEDGRLLASKC.VTDECFFFERLESNNYNTYRSRKY...  175
FGF4   VVSIFGVASRFFVAMSSKGKLYGSPF.FTDECTFKEILLPNNYNAYESYKY...  174
FGF6   VVSLFGVRSALFVAMNSKGRLYATPS.FQEECKFRETLLPNNYNAYESDLY...  176
FGF5   IVGIRGVFSNKFLAMSKKGKLHASAK.FTDDCKFRERFQENSYNTYASAIHRTE  182
FGF18  QVRIKGKETEFYLCMNRKGKLVGKPDGTSKECVFIEKVLENNYTALMSAKY...  146
FGF8   RVRVRGAETGLYICMNKKGKLIAKSNGKGKDCVFTEIVLENNYTALQNAKY...  146
FGF17  RVRIKGAESEKYICMNKRGKLIGKPSGKSKDCTFREEMDCLGYNQYRSMKH...  146
FGF15  TIAIKDVSVRYLCMSADGKIYGLIRYSEEDCTFREEMDCLGYNQYRSMKH...  146
FGF19  VHSVRYLCMGADGKMQGLLQYSEEDCAFEEEIRPDGYNVYRSEKH...  139
FGF21  VIQILGVKTSRFLCQRPDGALYGSLHFDPEACSFRELLLEDGYNVYQSEAH...  140
FGF23  FVVITGVMSRRYLCMDFRGNIFGSHYFDPENCRFQHQTLENGYDVYHSPQYHFL  135
              |____|  |____|      |____|           |____|
                5       6           7                 8         9
```

Figure 5A
CGGCAAAAAGGAGGGAATCCAGTCTAGGATCCTCACACCAGCTACTTGC
AAGGGAGAAGGAAAAGGCCAGTAAGGCCTGGGCCAGGAGAGTCCCGACA
GGAGTGTCAGGTTTCAATCTCAGCACCAGCCACTCAGAGCAGGGCACGA
TGTTGGGGGCCCGCCTCAGGCTCTGGGTCTGTGCCTTGTGCAGCGTCTG
CAGCATGAGCGTCCTCAGAGCCTATCCAATGCCTCCCCACTGCTCGGC
TCCAGCTGGGGTGGCCTGATCCACCTGTACACAGCCACAGCCAGGAACA
GCTACCACCTGCAGATCCACAAGAATGGCCATGTGGATGGCGCACCCCA
TCAGACCATCTACAGTGCCCTGATGATCAGATCAGAGGATGCTGGCTTT
GTGGTGATTACAGGTGTGATGAGCAGAAGATACCTCTGCATGGATTTCA
GAGGCAACATTTTTGGATCACACTATTTCGACCCGGAGAACTGCAGGTT
CCAACACCAGACGCTGGAAAACGGGTACGACGTCTACCACTCTCCTCAG
TATCACTTCCTGGTCAGTCTGGGCCGGGCGAAGAGAGCCTTCCTGCCAG
GCATGAACCCACCCCGTACTCCCAGTTCCTGTCCCGGAGGAACGAGAT
CCCCCTAATTCACTTCAACACCCCATACCACGGCGGCACACCCGGAGC
GCCGAGGACGACTCGGAGCGGGACCCCCTGAACGTGCTGAAGCCCCGGG
CCCGGATGACCCCGGCCCCGGCCTCCTGTTCACAGGAGCTCCCGAGCGC
CGAGGACAACAGCCCGATGGCCAGTGACCCATTAGGGGTGGTCAGGGGC
GGTCGAGTGAACACGCACGCTGGGGGAACGGGCCCGGAAGGCTGCCGCC
CCTTCGCCAAGTTCATCTAGGGTCGCTGGAAGGGCACCCTCTTTAACCC
ATCCCTCAGCAAACGCAGCTCTTCCCAAGGACCAGGTCCCTTGACGTTC
CGAGGATGGGAAAGGTGACAGGGGCATGTATGGAATTTGCTGCTTCTCT
GGGGTCCCTTCCACAGGAGGTCCTGTGAGAACCAACCTTTGAGGCCCAA
GTCATGGGGTTTCACCGCCTTCCTCACTCCATATAGAACACCTTTCCCA
ATAGGAAACCCCAACAGGTAAACTAGAAATTTCCCCTTCATGAAGGTAG
AGAGAAGGGGTCTCTCCCAACATATTTCTCTTCCTTGTGCCTCTCCTCT
TTATCACTTTTAAGCATAAAAAAAAAAAAAAAAAAAAAAAAAAAAAAAA
GCAGTGGGTTCCTGAGCTCAAGACTTTGAAGGTGTAGGGAAGAGGAAAT
CGGAGATCCCAGAAGCTTCTCCACTGCCCTATGCATTTATGTTAGATGC
CCCGATCCCACTGGCATTTGAGTGTGCAAACCTTGACATTAACAGCTGA
ATGGGGCAAGTTGATGAAAACACTACTTTCAAGCCTTCGTTCTTCCTTG
AGCATCTCTGGGGAAGAGCTGTCAAAGACTGGTGGTAGGCTGGTGAAA
ACTTGACAGCTAGACTTGATGCTTGCTGAAATGAGGCAGGAATCATAAT
AGAAAACTCAGCCTCCCTACAGGGTGAGCACCTTCTGTCTCGCT

Figure 5B
MLGARLRLWVCALCSVCSMSVLRAYPNASPLLGSSWGGLIHLYTATARN
SYHLQIHKNGHVDGAPHQTIYSALMIRSEDAGFVVITGVMSRRYLCMDF
RGNIFGSHYFDPENCRFQHQTLENGYDVYHSPQYHFLVSLGRAKRAFLP
GMNPPPYSQFLSRRNEIPLIHFNTPIPRRHTRSAEDDSERDPLNVLKPR
ARMTPAPASCSQELPSAEDNSPMASDPLGVVRGGRVNTHAGGTGPEGCR
PFAKFI

Figure 6A
AGCCTGTCTGGGAGTGTCAGATTTCAAACTCAGCATTAGCCACTCAGTG
CTGTGCAATGCTAGGGACCTGCCTTAGACTCCTGGTGGGCGTGCTCTGC
ACTGTCTGCAGCTTGGGCACTGCTAGAGCCTATCCGGACACTTCCCCAT
TGCTTGGCTCCAACTGGGGAAGCCTGACCCACCTGTACACGGCTACAGC
CAGGACCAGCTATCACCTACAGATCCATAGGGATGGTCATGTAGATGGC
ACCCCCCATCAGACCATCTACAGTGCCCTGATGATTACATCAGAGGACG
CCGGCTCTGTGGTGATAACAGGAGCCATGACTCGAAGGTTCCTTTGTAT
GGATCTCCACGGCAACATTTTTGGATCGCTTCACTTCAGCCCAGAGAAT
TGCAAGTTCCGCCAGTGGACGCTGGAGAATGGCTATGACGTCTACTTGT
CGCAGAAGCATCACTACCTGGTGAGCCTGGGCCGCGCCAAGCGCATCTT
CCAGCCGGGCACCAACCCGCCGCCCTTCTCCCAGTTCCTGGCTCGCAGG
AACGAGGTCCCGCTGCTGCATTTCTACACTGTTCGCCCACGGCGCCACA
CGCGCAGCGCCGAGGACCCACCGGAGCGCGACCCACTGAACGTGCTCAA
GCCGCGGCCCCGCGCCACGCCTGTGCCTGTATCCTGCTCTCGCGAGCTG
CCGAGCGCAGAGGAAGGTGGCCCCGCAGCCAGCGATCCTCTGGGGGTGC
TGCGCAGAGGCCGTGGAGATGCTCGCGGGGCGCGGGAGGCGCGGATAG
GTGTCGCCCCTTTCCCAGGTTCGTCTAGGTCCCCAGGCCAGGCTGCGTC
CGCCTCCATCCTCCAGTCGGTTCAGCCCACGTAGAGGAAGGACTAGGGT
ACCTCGAGGATGTCTGCTTCTCTCCCTTCCCTATGGGCCTGAGAGTCAC
CTGCGAGGTTCCAGCCAGGCACCGCTATTCAGAATTAAGAGCCAACGGT
GGGAGGCTGGAGAGGTGGCGCAGACAGTTCTCAGCACCCACAAATACCT
GTAATTCTAGCTCCAGGGGAATCTGTACTCACACACACACATCCACA
CACACACACACACATACATGTAATTTAAATGTTAATCTGATTTAAA
GACCCCAACAGGTAAACTAGACACGAAGCTCTTTTATTTTATTTTACT
AACAGGTAAACCAGACACTTGGCCTTTATTAGCCGGGTCTCTTGCCTAG
CATTTTAATCGATCAGTTAGCACGAGGAAAGAGTTCACGCCTTGAACAC
AGGGAAGAGGCCATCTCTGCAGCTTCTAGTTACTATTCTGGGATTCACG
GGTGTTTGAGTTTGAGCACCTTGACCTTAATGTCTTCACTAGGCAAGTC
GAAGAAAGACGCGCATTTCTTCTCTTTGGGAAGAGCTTTGGATTGGCGG
GAGGCTGACAAGGACACCTAAACCGAACACATTTCAGAGTTCAGCCTCC
CTGAGGAATGATTCGCCAATGATTCTGTGATAGGACCAGTCAGTAGCTT
TTGAATTTGCCCTGGCTCAGCAAAGTCTACCTTGCTAGGG

Figure 6B
MLGTCLRLLVGVLCTVCSLGTARAYPDTSPLLGSNWGSLTHLYTATART
SYHLQIHRDGHVDGTPHQTIYSALMITSEDAGSVVITGAMTRRFLCMDL
HGNIFGSLHFSPENCKFRQWTLENGYDVYLSQKHHYLVSLGRAKRIFQP
GTNPPPFSQFLARRNEVPLLHFYTVRPRRHTRSAEDPPERDPLNVLKPR
PRATPVPVSCSRELPSAEEGGPAASDPLGVLRRGRGDARGGAGGADRCR
PFPRFV

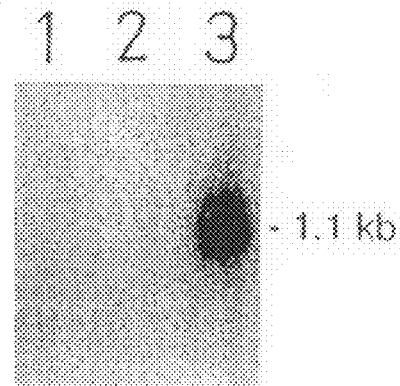
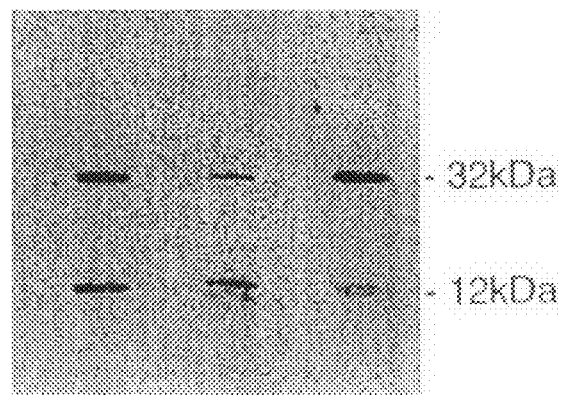

Figure 9

→ PREDICTED SIGNAL SEQUENCE

MLGARLRLWVCALCSVCSMSVLRAYPNASPLLGSSWGGLIHLYTATARNSY

HLQIHKNGHVDGAPHQTIYSALMIRSEDAGFVVITGVMSRRYLCMDFRGNI

FGSHYFDPENCRFQHQTLENGYDVYHSPQYHFLVSLGRAKRAFLPGMNPPP

PREDICTED PROTEASE CLEAVAGE SITE
YSQFLSRRNEIPLIHFNTPIPRRHTRSAEDDSERDPLNVLKPRARMTPA
                      176 179

PASCSQELPSAEDNSPMASDPLGVVRGGRVNTHAGGTGPEGCRPFAKFI

Figure 10B

NATIVE:    PIPRRHTRSAEDD
               176   179

R176Q:     PIPRQHTRSAEDD
               176   179

R179W:     PIPRRHTWSAEDD
               176   179

R179Q:     PIPRRHTQSAEDD
               176   179

KITS FOR DIAGNOSING A HYPOPHOSPHATEMIC DISORDER

CROSS-REFERENCE TO RELATED APPLICATIONS

This Application is a divisional of U.S. application Ser. No. 10/379,334, filed Mar. 4, 2003, now U.S. Pat. No. 7,314,618, which in turn is a divisional of U.S. patent application Ser. No. 09/901,938, now U.S. Pat. No. 7,223,563, filed Jul. 10, 2001, which is entitled to priority pursuant to 35 U.S.C. §119(e) to U.S. Provisional Patent Application 60/219,137, which was filed on Jul. 19, 2000.

STATEMENT REGARDING FEDERALLY SPONSORED RESEARCH OR DEVELOPMENT

The invention was made in part using funds obtained from the U.S. Government (National Institutes of Health Grant Nos. RO-1 AR42228, K24 AR02095, F32 AR08550) and the U.S. Government has certain rights in the invention.

BACKGROUND OF THE INVENTION

Conditions in which serum phosphate levels are reduced or elevated, referred to as hypophosphatemia and hyperphosphatemia, respectively, are associated with a large and diverse group of clinically significant diseases. Hypophosphatemia, which often results from renal phosphate wasting, is caused by a number of genetic disorders including X-linked hypophosphatemic rickets (XLH), hereditary hypophosphatemic rickets with hypercalciuria (HHRH), hypophosphatemic bone disease (HBD), and autosomal dominant hypopohsphatemic rickets (ADHR). Hyperphosphatemia, observed in patients with mild renal insufficiency and tumoral calcinosis, can often be associated with soft tissue calcification, secondary hyperparathyroidism, tertiary hyperparathyroidism, and other metabolic derangements.

The molecular mechanisms by which proper serum phosphate concentrations are maintained are poorly understood. Identification of genes responsible for inherited disorders involving disturbances in phosphate homeostasis may provide insight into the pathways that regulate phosphate balance. Currently, despite clinical features apparent in patients with hypophosphatemic and hyperphosphatemic conditions, molecular markers useful in early diagnosis, grading, and staging of these disorders are not available. Likewise, the current lack of effective methods of treatment for patients with hypophosphatemic and hyperphosphatemic disorders presents a need for alternative therapies. The present invention fulfills these needs.

BRIEF SUMMARY OF THE INVENTION

The invention includes an isolated nucleic acid encoding FGF23 or a mutant, variant, homolog, or fragment thereof.

In one aspect, the isolated nucleic acid encoding FGF23 shares at least about 50% sequence identity with a nucleic acid sequence of at least one of SEQ ID NO: 1 and SEQ ID NO:3.

The invention also includes an isolated nucleic acid encoding FGF23 wherein the isolated nucleic acid encodes a polypeptide having an amino acid sequence that shares at least 40% sequence identity with an amino acid sequence of at least one of SEQ ID NO:2 and SEQ ID NO:4.

In a preferred embodiment, the isolated nucleic acid of the invention is included in DSMZ Deposit No. DSM 13530.

In one aspect of the invention, the isolated nucleic acid encoding FGF23 is covalently linked to a nucleic acid encoding a tag polypeptide. In a preferred embodiment, the tag polypeptide is a myc tag polypeptide, a glutathione-S-transferase tag polypeptide, a green fluorescent protein tag polypeptide, a myc-pyruvate kinase tag polypeptide, a His6 tag polypeptide, an influenza virus hemagglutinin tag polypeptide, a flag tag polypeptide, or a maltose binding protein tag polypeptide.

The invention also includes a nucleic acid encoding FGF23, wherein the nucleic acid is operably linked to a nucleic acid specifying a promoter/regulatory sequence.

The invention further includes a vector comprising an isolated nucleic acid encoding FGF23. In a preferred embodiment, the vector comprises an isolated nucleic acid encoding FGF23 operably linked to a promoter/regulatory sequence.

The invention includes a recombinant cell comprising an isolated nucleic acid encoding FGF23 or a vector comprising the same.

The invention includes an isolated nucleic acid complementary to a nucleic acid encoding FGF23 or a mutant, variant, homolog, or fragment thereof, wherein the complementary nucleic acid is in an antisense orientation. In a preferred embodiment, the complementary nucleic acid shares at least 50% sequence identity with a nucleic acid complementary with a nucleic acid having the sequence of at least one of SEQ ID NO: 1 and SEQ ID NO:3. Also included in the invention is a vector comprising the antisense nucleic acid, as well as a vector comprising the antisense nucleic acid operably linked to a nucleic acid specifying a promoter/regulatory sequence.

The invention further includes a recombinant cell comprising the antisense nucleic acid and vectors comprising the same.

The invention includes a transgenic non-human mammal comprising an isolated nucleic acid encoding FGF23 or a mutant, variant, homolog, or fragment thereof.

The invention further includes an isolated polypeptide comprising FGF23 or a mutant, variant, homolog, or fragment thereof. In a preferred embodiment, the isolated polypeptide shares at least about 40% sequence identity with an amino acid sequence of at least one of SEQ ID NO:2 and SEQ ID NO:4.

The invention includes an antibody that specifically binds with an FGF23 polypeptide, or a mutant, variant, homolog, or fragment thereof. In a preferred embodiment, the antibody is a polyclonal antibody, a monoclonal antibody, a humanized antibody, a chimeric antibody, or a synthetic antibody.

The invention further includes an isolated nucleic acid encoding FGF23, wherein the nucleic acid comprises a mutation. In a preferred embodiment, the mutation confers increased stability on FGF23. More preferably, the mutation affects amino acid 176 (arginine) relative to SEQ ID NO:2 or amino acid 179 (arginine) relative to SEQ ID NO:2. Even more preferably, the mutation is selected from the group consisting of 527G>A, 535C>T and 536G>A relative to SEQ ID NO:1.

The invention also includes an FGF23 polypeptide comprising a mutation. In a preferred embodiment, the FGF23 polypeptide comprises a mutation that confers increased stability. More preferably, the mutation is at amino acid 176 (arginine) relative to SEQ ID NO:2 or a mutation at amino acid 179 (arginine) relative to SEQ ID NO:2.

The invention includes an inhibitor of FGF23. The inhibitor can be a molecule that reduces the level of mRNA encoding FGF23 polypeptide, a molecule that reduces the level of FGF23 polypeptide, or a molecule that reduces a biological activity of FGF23. In a preferred embodiment, the inhibitor is an antisense nucleic acid, a ribozyme, an antibody, a peptide, or a peptidomimetic. More preferably, the inhibitor is an antibody that specifically binds with FGF23 or an antibody that specifically binds with an FGF23 receptor.

The invention includes a composition comprising an isolated nucleic encoding FGF23 and a pharmaceutically-acceptable carrier.

The invention also includes a composition comprising an isolated nucleic acid complementary to a nucleic acid encoding FGF23 and a pharmaceutically-acceptable carrier.

The invention also includes a composition comprising an isolated FGF23 polypeptide and a pharmaceutically-acceptable carrier.

The invention also includes a composition comprising an antibody that specifically binds with FGF23 and a pharmaceutically-acceptable carrier.

The invention also includes a composition comprising an isolated nucleic acid encoding a mutant form of FGF23 and a pharmaceutically-acceptable carrier.

The invention also includes a composition comprising an isolated nucleic acid encoding a mutant form of FGF23 with increased stability and a pharmaceutically-acceptable carrier.

The invention also includes a composition comprising an isolated nucleic acid encoding a mutant form of FGF23 comprising a mutation at amino acid 176 (arginine) relative to SEQ ID NO:2 or a mutation at amino acid 179 (arginine) relative to SEQ ID NO:2 and a pharmaceutically-acceptable carrier.

The invention also includes a composition comprising an isolated FGF23 polypeptide comprising a mutation and a pharmaceutically-acceptable carrier.

The invention also includes a composition comprising an isolated FGF23 polypeptide comprising a mutation which confers increased stability and a pharmaceutically-acceptable carrier.

The invention also includes a composition comprising an isolated FGF23 polypeptide comprising a mutation at amino acid 176 (argininc) relative to SEQ ID NO:2 or a mutation at amino acid 179 (arginine) relative to SEQ ID NO:2 and a pharmaceutically-acceptable carrier.

The invention also includes a composition comprising an inhibitor of FGF23 and a pharmaceutically-acceptable carrier.

The invention further includes a method of diagnosing a hypophosphatemic disorder in a mammal. The method comprises (a) obtaining a biological sample from said mammal and (b) contacting said biological sample with a reagent which detects the presence or absence of a mutation in a nucleic acid encoding FGF23, wherein the presence of a mutation is an indication that the mammal is afflicted with the hypophosphatemic disorder, thereby diagnosing the hypophosphatemic disorder in the mammal.

In a preferred embodiment, the hypophosphatemic disorder is autosomal dominant hypophosphatemic rickets (ADHR).

In another preferred embodiment, the biological sample blood or urine.

In yet another preferred embodiment, the reagent is a nucleic acid. More preferably, the reagent is detectably labeled. Preferable labels include a radioisotope, a bioluminescent compound, a chemiluminescent compound, a fluorescent compound, a metal chelate, and an enzyme.

The invention includes a method of diagnosing a hypophosphatemic disorder in a mammal. The method comprises (a) obtaining a biological sample from said mammal and (b) contacting the biological sample with a reagent which detects the presence or absence of a mutant form of FGF23 polypeptide, wherein the presence of a mutant form of FGF23 polypeptide is an indication that the mammal is afflicted with the hypophosphatemic disorder, thereby diagnosing the hypophosphatemic disorder in the mammal.

In a preferred embodiment, the hypophosphatemic disorder is autosomal dominant hypophosphatemic rickets (ADHR).

In another preferred embodiment, the biological sample blood or urine.

In yet another preferred embodiment, the reagent is an antibody.

The invention includes a method of diagnosing a hypophosphatemic disorder in a mammal. The method comprises (a) obtaining a biological sample from said mammal and (b) contacting the biological sample with a reagent that detects the level of FGF23 polypeptide in the sample, wherein an elevated level of FGF23 polypeptide in the sample, relative to the level of FGF23 polypeptide in a control mammal, is an indication that the mammal is afflicted with the hypophosphatemic disorder, thereby diagnosing the hypophosphatemic disorder in the mammal.

In a preferred embodiment, the hypophosphatemic disorder is selected from the group consisting of X-linked hereditary rickets (XLH), hereditary hypophosphatemic rickets (HHRH), hypophosphatemic bone disease (HBD), autosomal dominant hypophosphatemic rickets (ADHR), tumor induced osteomalacia, epidermal nevus syndrome, fibrous dysplasia, or nephrolithiasis.

In another preferred embodiment, the biological sample is blood or urine.

In yet another preferred embodiment, the reagent is an FGF23 antibody. More preferably, the reagent is detectably labeled. Preferable labels include a radioisotope, a bioluminescent compound, a chemiluminescent compound, a fluorescent compound, a metal chelate, and an enzyme.

The invention further includes a method of diagnosing tumor induced osteomalacia in a patient. The method comprises (a) obtaining a tumor sample from the patient and (b) detecting the expression or lack thereof of FGF23 in the tumor, wherein the expression of FGF23 is indicative that the patient has tumor induced osteomalacia.

The invention also includes a method of treating a hypophosphatemic disorder in a mammal. The method comprises administering to a mammal afflicted with the disorder a therapeutically effective amount of an FGF23 inhibitor. The inhibitor can be an inhibitor which reduces the level of mRNA encoding FGF23 polypeptide in said mammal, an inhibitor which reduces the level of FGF23 polypeptide in said mammal, or an inhibitor of the biological activity of FGF23 in said mammal.

In a preferred embodiment, the hypophosphatemic disorder X-linked hereditary rickets (XLH), hereditary hypophosphatemic rickets (HHRH), hypophosphatemic bone disease (HBD), autosomal dominant hypophosphatemic rickets (ADHR), tumor induced osteomalacia, epidermal nevus syndrome, fibrous dysplasia, or nephrolithiasis.

In another preferred embodiment, the inhibitor is an antisense nucleic acid, a ribozyme, an antibody, a peptide, or a peptidomimetic.

The invention further includes a method of treating a hyperphosphatemic disorder in a mammal. The method comprises administering to a mammal afflicted with the disorder a therapeutically effective amount of an isolated nucleic acid encoding FGF23.

In a preferred embodiment, the isolated nucleic acid comprises a mutation that confers increased stability on the FGF23 polypeptide encoded thereby.

In another preferred embodiment, the hyperphosphatemic disorder mild renal insufficiency or tumoral calcinosis.

The invention also includes a method of treating a hyperphosphatemic disorder in a mammal. The method comprises administering to a mammal afflicted with the disorder a therapeutically effective amount of an isolated FGF23 polypeptide.

In a preferred embodiment, the isolated FGF23 polypeptide comprises a mutation that confers increased stability.

In another preferred embodiment, the hyperphosphatemic disorder mild renal insufficiency or tumoral calcinosis.

The invention further includes a method of treating a hyperphosphatemic disorder in a mammal. The method comprises administering to the mammal afflicted with the disorder a therapeutically effective amount of a reagent that increases the level of FGF23 polypeptide is the mammal.

In a preferred embodiment, the reagent inhibits degradation of FGF23 polypeptide.

In another preferred embodiment, the hyperphosphatemic disorder mild renal insufficiency or tumoral calcinosis.

The invention further includes a method of treating a hyperphosphatemic disorder in a mammal. The method comprises administering to a mammal afflicted the disorder a therapeutically effective amount of a population of cells comprising an isolated nucleic acid encoding FGF23.

In a preferred embodiment, the isolated nucleic acid comprises a mutation that confers increased stability on the FGF23 encoded thereby.

In another preferred embodiment, the hypophosphatemic disorder mild renal insufficiency or tumoral calcinosis.

The invention includes a method of treating osteoporosis in a mammal. The method comprises administering to the mammal a therapeutically effective amount of a FGF23 or a reagent that increases the level of FGF23 polypeptide in the mammal.

The invention further includes a method of treating a condition involving deposition of calcium and phosphate in the arteries or soft tissues of a mammal. The method comprises administering to the mammal a therapeutically effective amount of FGF23 or a reagent that increases the level of FGF23 polypeptide.

In a preferred embodiment, the condition is dermatomyositis.

The invention further includes a method of treating coronary artery disease in a mammal. The method comprises administering to the cells of the coronary artery of an afflicted mammal a nucleic acid encoding a FGF23.

The invention also includes a kit for diagnosing a hypophosphatemic disorder in a mammal. The kit comprises a reagent which detects the presence or absence of a mutation in the nucleic acid sequence encoding FGF23 wherein the presence of the mutation is an indication that the mammal is afflicted with the hypophosphatemic disorder. The kit further comprises an applicator and an instructional material for the use thereof.

The invention also includes a kit for diagnosing a hypophosphatemic disorder in a mammal. The kit comprises a reagent that detects the level of FGF23 polypeptide, wherein an elevated level of FGF23 polypeptide is an indication that the mammal is afflicted with the hypophosphatemic disorder. The kit further comprises an applicator and an instructional material for the use thereof.

The invention also includes a kit for diagnosing a hypophosphatemic disorder in a mammal. The kit comprises a reagent which detects the presence or absence of a mutant form of a FGF23 polypeptide, wherein the presence of the mutant form of FGF23 is an indication that the mammal is afflicted with the hypophosphatemic disorder. The kit further comprises an applicator and an instructional material for the use thereof.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIG. 1A is a diagram depicting linkage analysis within the pedigrees of two different ADHR families (1406 and 1478).

FIGS. 3A through 3C are an amino acid sequence alignment of FGF23 and other mammalian FGF family members (SEQ ID NOS: 14-34 in the order in which they appear in the figure). The alignment is confined to the core sequence which consists of twelve antiparallel beta strands. The locations of the segments with beta-sheet conformation in the FGF-2 crystal structure are underlined. The two arginines which are mutated in FGF23 (FIG. 3C; indicated by asterisks) are conserved within the mouse homolog of FGF23. The alignment was generated with CLUSTAL and PRETTYBOX. Human and mouse FGF23 were identified by the FGF profile of the PFAM database (4.6e-14, 1.9e-16). They share 25% to 36% amino acid identity with the other members of the FGF family in the common core sequence.

FIG. 5A is the cDNA sequence of human FGF23 (SEQ ID NO:1).

FIG. 5B is the amino acid sequence of human FGF23 (SEQ ID NO:2).

FIG. 6A is the cDNA sequence of mouse FGF23 (SEQ ID NO:3).

FIG. 6B is the amino acid sequence of mouse FGF23 (SEQ ID NO:4).

FIG. 7A is an image of a Western blot depicting in vitro expression of bacterially-produced FGF23. The anti-FGF23 antibody recognized a protein of 27 kDa from IPTG-induced (+) but not non-induced (−) bacteria transformed with histidine-tagged FGF23 (FGF23-6×His).

FIG. 7B is an image of a Northern blot depicting expression of FGF23 from transfected cells. Northern blot analysis of total RNA from HEK293 cells transfected with an FGF23-expressing vector (pFGF23; lane 3) using an FGF23 probe revealed a single transcript of 1.1 kb. (Lane 1=untransfected HEK293 cells; lane 2=HEK293 cells transfected with control vector, pcDNA3.1.)

FIG. 7C is an image of a Western blot depicting secretion of FGF23 from transfected cells. Anti-FGF23 antibody recognized two protein bands of 32 and 12 kDa in concentrated conditioned media obtained from cells transfected with pFGF23 (lanes 2, 4, 6), but not from untransfected cells (lanes 1, 3, 5).

FIG. 9 is the amino acid sequence of human FGF23 (SEQ ID NO:2) where the predicted signal peptide and RXXR/S (SEQ ID NO:35) protease cleavage sites are indicated.

FIG. 10B is a listing of wild-type and ADHR mutant (R176Q, R179W, R179Q) forms of human FGF23 from amino acids 172 to 184.

DETAILED DESCRIPTION OF THE INVENTION

Figure 1B:
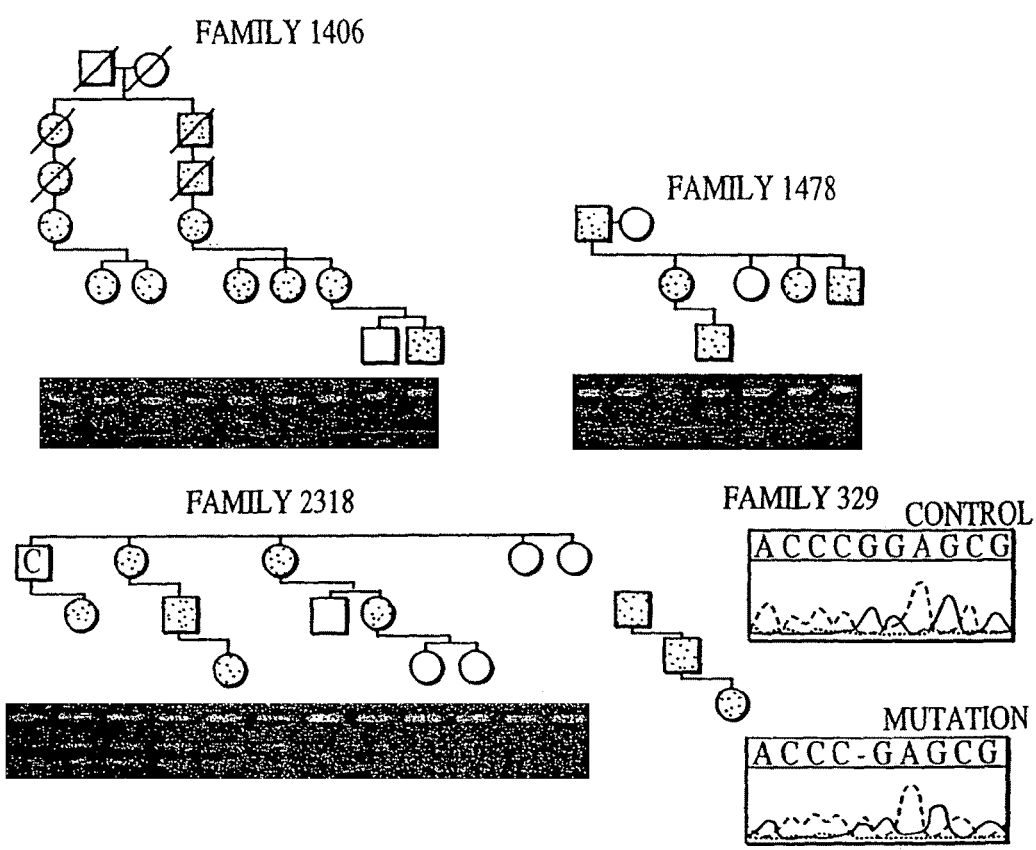
FIG. 1B is a series of diagrams of pedigrees and images of agarose gels depicting mutation analysis in three different ADHR families (1406, 1478, and 2318).

The invention relates to the discovery of a novel nucleic acid encoding a mammalian fibroblast growth factor-23 (FGF23) and proteins encoded thereby. The invention discloses a novel member of the fibroblast growth factor family in which the nucleic acid and protein encoded thereby are useful for the development of diagnostic and therapeutic reagents for the diagnosis and treatment of hypophosphatemic and hyperphosphatemic disorders.

The kidney plays a major role in maintaining proper serum phosphate concentrations. The identification of genes that cause rare heritable disorders of impaired phosphate regulation provide an opportunity to discover renal pathways that control mineral ion balance.

In the initial experiments disclosed herein, the gene responsible for autosomal dominant hypophosphatemic rickets (ADHR) has been discovered and has been named FGF23. ADHR is characterized by short stature, bone pain, fracture and lower extremity deformity. It has also been discovered herein that FGF23 is overexpressed in tumors that lead to oncogenic hypophosphatemic osteomalacia, an acquired disorder of renal phosphate wasting. Patients with oncogenic hypophosphatemic osteomalacia share biochemical and clinical similarities with ADHR patients. These are but two of several hypophosphatemic diseases which may be treated by reducing the level and/or activity of FGF23 in a patient. Other hypophosphatemic diseases amenable to treatment with inhibitors of FGF23 include, but are not limited to, XLH, HHRH, HBD, epidermal nevus syndrome, fibrous dysplasia, nephrolithiasis, and the like.

Unlike hypophosphatemic diseases which are characterized by renal phosphate wasting and low serum phosphate, hyperphosphatemic diseases, including mild renal insufficiency, tumoral calcinosis and the like, are characterized by an excess of phosphate in the serum. Administration of FGF23 stimulates excretion of phosphate in the urine and thereby reduces phosphate levels in the serum. Thus, hyperphosphatemic diseases can be treated by administering native FGF23 or molecules that increase the level of FGF23 polypeptide in a patient. In addition, mutant FGF23 may also be used to treat hyperphosphatemia, particularly in situations where the mutant has a longer half life than native FGF23. Specific mutants of FGF23 having a longer half life are disclosed herein.

Thus, it has been discovered in the present invention that FGF23 may be involved in both hypophosphatemic and hyperphosphatemic conditions in animals. Essentially, when the level of FGF23 in an animal is abnormally elevated, generally when the protein is overexpressed or has increased ability due to genetic mutation, the animal exhibits hypophosphatemia due to increased phosphate wasting. Whereas it has not yet been determined whether abnormal levels of FGF23 play a causative role in hyperphosphatemia, the ability of FGF23 to decrease serum phosphate levels in an animal is a clear indication that FGF23 plays an important role in the regulation of phosphate homeostasis.

The invention includes an isolated nucleic acid encoding FGF23. As disclosed herein, an isolated nucleic acid encoding FGF23 has been isolated from both human cells and murine cells (see for example, FIGS. 5A and 6A; SEQ ID NO:1 and SEQ ID NO:3, respectively). The preferred nucleic acid encoding FGF23 is DNA. In addition, although human and murine FGF23 nucleic acid and protein are exemplified herein, the invention should not be construed to be limited solely to FGF23 obtained from these species of mammal. Rather, the invention should be construed to include any isolated nucleic acid encoding FGF23 or any mutant, variant, or homolog thereof, having the biological activity of FGF23 as defined herein. Preferably the DNA encoding FGF23 of the invention shares about 50% homology with SEQ ID NO:1 or SEQ ID NO:3. More preferably, the DNA shares about 60%, even more preferably, the DNA shares about 70%, yet more preferably, the DNA shares about 80%, more preferably 90%, yet more preferably 95% and even more preferably the DNA shares about 99-100% homology with SEQ ID NO:1 or SEQ ID NO:3.

The invention includes a nucleic acid encoding FGF23 wherein a nucleic acid encoding a tag polypeptide is covalently linked thereto. That is, the invention encompasses a chimeric nucleic acid wherein the nucleic acid sequences encoding a tag polypeptide is covalently liked to the nucleic acid encoding the FGF23 polypeptide. Such tag polypeptides are well known in the art and include, for instance, green fluorescent protein (GFP), myc, myc-pyruvate kinase (myc-PK), His$_6$, maltose biding protein (MBP), an influenza virus hemagglutinin tag polypeptide, a flag tag polypeptide (FLAG), and a glutathione-S-fransferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The nucleic acid comprising a nucleic acid encoding a tag polypeptide can be used to localize FGF23 within a cell, a tissue, and/or a whole organism (e.g., a mammalian embryo), detect FGF23 secreted from a cell, and to study the role(s) of FGF23 in a cell. Further, addition of a tag polypeptide facilitates isolation and purification of the "tagged" protein such that the proteins of the invention can be produced and purified readily.

Also included in the invention is a nucleic acid encoding FGF23 wherein a nucleic acid specifying a promoter/regulatory sequence is operably linked thereto. Preferably, the nucleic acid specifying the promoter/regulatory is positioned at the 5' end of FGF23 coding sequence such that it drives expression of the desired protein in a cell.

In other related aspects, the invention includes a vector which comprises an isolated nucleic acid encoding FGF23. Preferably, the vector is capable of directing expression of FGF23 in a vector-containing cell. Vectors suitable for use in the present invention include, but are not limited to, vectors which facilitate the generation of multiple copies of nucleic acid encoding FGF23 or which facilitate expression of FGF23 protein in either prokaryotic or eukaryotic cells or both. Thus, the invention should not be construed to be limited to any known vector system, but rather should include all suitable known or heretofore unknown vectors which facilitate the generation of multiple copies of FGF23 encoding nucleic acid, or which facilitate the expression of FGF23 in a cell. Examples of suitable vectors include bacteriophage T7-based expression vectors for replication and expression in bacteria, the pMSXND expression vector for replication and expression in mammalian cells and baculovirus-derived vectors for replication and expression in insect cells. Adenoviruses, retrovirus and other viral vectors are also contemplated in the invention.

Preferably, the isolated nucleic acid molecule of the invention is operably linked to promoter/regulatory elements and other regulatory elements, such as stop signals, polyadenylation signals and the like, in the recombinant vector of the invention, each of which guarantee efficient replication and expression of FGF23 in the cells. The invention should not be limited to any specific promoter/regulatory sequence which drives expression of FGF23. Rather, the invention should be construed to include any and all suitable promoter/regulatory sequences which can be operably linked to nucleic acid encoding FGF23 and effect the expression of FGF23 therefrom in any desired eukaryotic or prokaryotic cell. Techniques for the linking of suitable promoter sequences to a nucleic acid are well known in the art and are described, for example, in Sambrook et al. (1989, Molecular Cloning: A Laboratory Manual, Cold Spring Harbor Laboratory, New York), in Ausubel et al. (1997, Current Protocols in Molecular Biology, John Wiley & Sons, New York), and in Gerhardt et al. (eds., 1994, Methods for General and Molecular Bacteriology, American Society for Microbiology, Washington, D.C.).

The invention further includes a cell containing the vector of the invention, wherein the cell is either a prokaryotic or a eukaryotic cell, i.e., a mammalian, bacterial, insect or yeast cell, for example. FGF23 protein may be produced using such vector-containing cells, as described herein. Again, the invention should not be construed to be limited to the particular types of cell used to express FGF23.

The invention further includes an isolated nucleic acid having a sequence which is in the antisense orientation (i.e. is complementary) to all or a portion of the isolated nucleic acid encoding FGF23. In one aspect, the invention includes an antisense RNA sequence characterized in that it can bind to mRNA encoding FGF23 and thereby inhibit synthesis of FGF23. Again, vectors, including those in which the nucleic acid is operatively linked to promoter/regulatory elements, and cells comprising an antisense FGF23 isolated nucleic acid sequence are contemplated in the invention.

In another aspect, the invention includes a ribozyme comprising an RNA sequence complementary to the mRNA encoding FGF23 wherein the ribozyme is thereby able to bind to and cleave the mRNA and inhibit synthesis of FGF23 encoded by the mRNA. Ribozymes are composed of a single-stranded RNA chain which can intermolecularly cleave a target RNA, for example, FGF23 mRNA. It is possible to construct a ribozyme which can cleave RNA at a specific target site following procedures described in the art (e.g., Tanner et al., IN: Antisense Research and Applications, CRC Press INC. 1993, pp 415-426). The two main requirements for such ribozomes are the catalytic domain and regions which are complementary to the target RNA and which allow them to bind to the substrate (a prerequisite for cleavage). Antisense RNA and ribozymes are useful as inhibitors of FGF23 expression. Preferably, the antisense RNA and ribozyme of the invention are complementary to the 5' end of mRNA encoding FGF23. One of skill in the art of generating antisense fragments and ribozymes will know, based upon the sequence provided herein, precisely which FGF23 mRNA sequences can be targeted by antisense molecules or ribozymes to effect inhibition of FGF23 expression.

There are two basic types of ribozomes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules.

Ribozymes useful for inhibiting the expression of FGF23 may be designed by incorporating target sequences into the basic ribozyme structure which are complementary to the mRNA sequence of the FGF23 encoded by FGF23 or having at least about 50% sequence identity with at least one of SEQ ID NO: 1 and SEQ ID NO:3. Ribozymes targeting FGF23 may be synthesized using commercially available reagents (Applied Biosystems, Inc., Foster City, Calif.) or they may be genetically expressed from DNA encoding them.

The invention further includes a non-human transgenic mammal the genome of which lacks a functional form of FGF23, and thereby eliminates the biological activity of FGF23. In one example, the non-human transgenic mammal comprises an exogenous nucleic acid inserted into a desired site in the genome thereof thereby deleting the coding region FGF23, i.e., a knock-out transgenic mammal. Such animals provide a useful model to study human disease states associated with mutations in FGF23. Preferably, the transgenic mammal is a mouse. A mouse in which the function of FGF23 has been knocked out would either have a hyperphosphatemic phenotype or a non-phosphate phenotype.

Further, the invention includes a transgenic non-human mammal wherein an exogenous nucleic acid encoding FGF23 is inserted into a site the genome, i.e., a "knock-in" transgenic mammal. The knock-in transgene inserted may comprise various nucleic acids encoding, for example, a tag polypeptide, a promoter/regulatory region operably linked to the nucleic acid encoding FGF23 not normally present in the cell or not typically operably linked to FGF23. Expression of the FGF23 knock-in transgene likely cause hypophosphatemia in the animal, resulting in a phenotype which resembles oncogenic hypophosphatemic osteomalacia and ADHR. Both wild-type and mutant forms of FGF23 can be inserted into the genome of the mammal. In particular, insertion of the mutants disclosed herein would produce a more stable form of FGF23 and may therefore result in a prolonged or enhanced hypophosphatemic condition in the animal.

The generation of the non-human transgenic mammal of the invention is preferably accomplished using the method which is now described. However, the invention should in no way be construed as being limited solely to the use of this method, in that, other methods can be used to generate the desired knock-out mammal.

In the preferred method of generating a non-human transgenic mammal, ES cells are generated comprising the transgene of the invention and the cells are then used to generate the knock-out animal essentially as described in Nagy and Rossant (1993, In: Gene Targeting, A Practical Approach, pp. 146-179, Joyner ed., IRL Press). ES cells behave as normal embryonic cells if they are returned to the embryonic environment by injection into a host blastocyst or aggregate with blastomere stage embryos. When so returned, the cells have the full potential to develop along all lineages of the embryo. Thus, it is possible, to obtain ES cells, introduce a desired DNA therein, and then return the cell to the embryonic environment for development into mature mammalian cells, wherein the desired DNA may be expressed.

Precise protocols for the generation of transgenic mice are disclosed in Nagy and Rossant (1993, In: Gene Targeting, A Practical Approach, Joyner ed. IRL Press, pp. 146-179). and are therefore not repeated herein. Transfection or transduction of ES cells in order to introduce the desired DNA therein is accomplished using standard protocols, such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York). Preferably, the desired DNA contained within the transgene of the invention is electroporated into ES cells, and the cells are propagated as described in Soriano et al. (1991, Cell 64:693-702).

Introduction of an isolated nucleic acid into the fertilized egg of the mammal is accomplished by any number of standard techniques in transgenic technology (Hogan et al., 1986, Manipulating the Mouse Embryo: A Laboratory Manual, Cold Spring Harbor, N.Y.). Most commonly, the nucleic acid is introduced into the embryo by way of microinjection.

Once the nucleic acid is introduced into the egg, the egg is incubated for a short period of time and is then transferred into a pseudopregnant mammal of the same species from which the egg was obtained as described, for example, in Hogan et al. (1986, Manipulating the Mouse Embryo: A Laboratory Manual, Cold Spring Harbor, N.Y.). Typically, many eggs are injected per experiment, and approximately two-thirds of the eggs survive the procedure. About twenty viable eggs are then transferred into pseudopregnant animals, and usually four to ten of the viable eggs so transferred will develop into live pups.

Any mammalian FGF23 gene may be used in the methods described herein to produce a transgenic mammal or a transgenic cell harboring a transgene comprising a deletion of all or part of that FGF23 gene. Preferably, an FGF23 gene such as, e.g., mouse FGF23 (SEQ ID NO:3), is used, and human FGF23 (SEQ ID NO: 1) gene, is also used.

The transgenic mammal of the invention can be any species of mammal. Thus, the invention should be construed to include generation of transgenic mammals encoding the chimeric nucleic acid, which mammals include mice, hamsters, rats, rabbits, pigs, sheep and cattle. The methods described herein for generation of transgenic mice can be analogously applied using any mammalian species. Preferably, the transgenic mammal of the invention is a rodent and even more preferably, the transgenic mammal of the invention is a mouse. By way of example, Lukkarinen et al. (1997, Stroke 28:639-645), teaches that gene constructs which enable the generation of transgenic mice also enable the generation of other transgenic rodents, including rats. Similarly, nullizygous mutations in a genetic locus of an animal of one species can be replicated in an animal of another species having a genetic locus highly homologous to the first species.

To identify the transgenic mammals of the invention, pups are examined for the presence of the isolated nucleic acid using standard technology such as Southern blot hybridization, PCR, and/or RT-PCR. Expression of the nucleic acid in the cells and in the tissues of the manurial is also assessed using ordinary technology described herein. Further, the presence or absence of FGF23 in the circulating blood of the transgenic animal can be determined, for example, as disclosed herein (e.g., Western blot analysis), or using standard methods for protein detection that are well-known in the art.

Cells obtained from the transgenic mammal of the invention, which are also considered "transgenic cells" as the term is used herein, encompass cells such as those obtained from the FGF23 (+/−) and (−/−) transgenic non-human mammal described elsewhere herein, are useful systems for modeling diseases and symptoms of mammals which are believed to be associated with altered levels of FGF23 expression.

Particularly suitable are cells derived from a tissue of the non-human knock-out or knock-in transgenic mammal described herein, wherein the transgene comprising the FGF23 gene is expressed or inhibits expression of FGF23 in various tissues. By way of example, cell types from which such cells are derived include fibroblasts and endothelial cells of (1) the FGF23 (+/+), (+/−) and (−/−) non-human transgenic liveborn mammal, (2) the FGF23 (+/+), (−/−) or (+/−) fetal animal, and (3) placental cell lines obtained from the FGF23 (+/+), (−/−) and (+/−) fetus and liveborn mammal.

The invention additionally includes an isolated polypeptide encoded by FGF23 nucleic acid. The amino acid sequence encoded by human and mouse FGF23 DNA is provided herein in FIGS. 5B and 6B as SEQ ID NO:2 and SEQ ID NO:4, respectively. As stated above, the invention should in no way be construed to be limited to FGF23 isolated from human and murine species. Rather, the invention should be construed to include any isolated FGF23 polypeptide or any mutant, variant, or homolog thereof, having the biological activity of FGF23 as defined herein.

While the preferred amino acid sequence of human FGF23 protein is SEQ ID NO:2 and mouse FGF23 protein is SEQ ID NO:4, the invention should not be construed to be limited to these sequences. Rather, the amino acid sequence of human and mouse FGF23 should be construed to be any mutant, variant, or homolog thereof, having the biological activity of FGF23 as described herein. Preferably the amino acid sequence of FGF23 shares about 40% sequence identity with SEQ ID NO:2 or SEQ ID NO:4. More preferably, the amino acid sequence shares about 50%, even more preferably, the amino acid sequence shares about 60%, yet more preferably, the amino acid sequence shares about 70%, more preferably 80%, even more preferably 90%, yet more preferably 95% and even more preferably the amino acid sequence shares about 99-100% homology with SEQ ID NO:2 or SEQ ID NO:4.

The present invention also provides for analogs of proteins or peptides encoded by an FGF23 gene. Analogs, as defined herein, can differ from naturally occurring protein or peptides by conservative amino acid sequence differences or by modifications which do not affect sequence, or by both.

In addition to full length peptides, the invention provides for peptides having the 10 biological activity of FGF23, as defined herein. One skilled in the art would appreciate, based on the sequences disclosed herein, that overlapping fragments of FGF23 can be generated using standard recombinant technology, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York). One skilled in the art would appreciate, based on the disclosure presented herein, that the biological activity of FGF23 fragments could be tested by injecting the material into mice and evaluating whether injected mice exhibit phosphate wasting. Induction of phosphate wasting would serve as an indication that the FGF23 fragment retained biological activity. In addition, in vitro assays can be used to test FGF23 biological activity. For example, isolated renal tubules may be perfused with FGF23 fragments and evaluated for alterations in phosphate transport, relative to wild type FGF23. Similarly, cell culture models which possess the necessary FGF23 signal transduction machinery (i.e. FGF receptor and sodium transporter) may be transfected with FGF23 fragments and subsequently tested for alterations in phosphate transport, relative to wild type FGF23.

As stated above, the present invention also provides for analogs of proteins or peptides encoded by FGF23. Analogs can differ from naturally occurring proteins or peptides by conservative amino acid sequence differences or by modifications which do not affect sequence, or by both. Any number of procedures may be used for the generation of mutant, derivative or variant forms of FGF23 using recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York).

For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine (in positions other than proteolytic enzyme recognition sites);
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

By the term "biological activity of FGF23" as used herein is meant the ability of a molecule to bind to an FGF receptor and alter phosphate transport in vivo or in vitro. The skilled artisan would further appreciate, based upon the instant disclosure, that the invention is not limited to any particular method of assessing the activity of FGF23 and that the invention encompasses any assay to assess the activity of FGF23 known in the art or to be developed in the future.

The present invention not only provides for isolated FGF23 proteins, peptides and analogs and fragments thereof, but also provides methods of their production. In one aspect of the invention, FGF23 proteins, peptides and analogs and fragments thereof, are produced by cultivating a vector-containing cell, wherein the vector comprises FGF23 nucleic acid, under conditions which allow synthesis of the protein. Isolation and purification of recombinantly-produced FGF23 proteins, polypeptides, fragments, etc, may be carried out by conventional means including chromatography, affinity and immunology-based separations, e.g. using an anti-FGF23 antibody. Each of these methods is described in standard text books, such as, for example, in Sambrook et al. (1989, Molecular Cloning: A Laboratory Manual, Cold Spring Harbor Laboratory, New York), in Ausubel et al. (1997, Current Protocols in Molecular Biology, John Wiley & Sons, New York), and in Gerhardt et al. (eds., 1994, Methods for General and Molecular Bacteriology, American Society for Microbiology, Washington, D.C.).

The invention further includes an antibody that specifically binds with FGF23, or a fragment thereof. In a preferred embodiment, the invention includes an antibody that inhibits the biological activity of FGF23. The antibody is useful for the identification for FGF23 in a diagnostic assay for the determination of the levels of FGF23 in a mammal having a disease associated with FGF23 levels. In addition, an antibody that specifically binds FGF23 is useful for blocking the interaction between FGF23 and its cognate receptor, and is therefore useful in a therapeutic setting for treatment of FGF23 related disease, as described herein.

Two receptors for FGF23 have been identified and include FGFR2 and FGFR4; however, there is no reason to believe that these are the only two FGF23 receptors. To identify other FGF receptors, the following assays may be employed. Binding of FGF23 to its receptor can be detected using standard protein binding assays, including the use of immobilized protein A to precipitate commercially available FGF receptor-Fc chimeras. Additionally, expression libraries may be screened by standard methods known in the art to detect binding of FGF23 to receptors other than those known to bind FGFs. Thus, by following the experiments provided herein, other FGF23 receptors may be identified.

Administration of FGFR2 and FGFR4 or other FGF23 receptors to a patient, either by genetic or non-genetic means described herein, may inhibit the interaction and subsequent activation of FGF23, and thereby treat hypophosphatemia. Likewise, antibodies and other small molecules that block the interaction of FGF23 and its receptor may also function to inhibit FGF23 activity, either by binding to FGF23 or to its receptor. One skilled in the art would appreciate, based on the disclosure presented herein, that FGF23 receptor blockers can be identified by screening compounds for their ability to block the FGF23-receptor interaction using one of many well-characterized protein binding assays.

The generation of antibodies that specifically bind to FGF23 is described in the experimental details section here. However, the invention should not be construed to be limited solely to those antibodies specifically disclosed herein, but rather should include any and all antibodies which can be made that specifically bind to FGF23. For example, the generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. in Immunol. 12(3, 4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule.

However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995; J. Mol. Biol. 248:97-105).

The invention further includes mutant forms of FGF23. That is, the invention encompasses isolated nucleic acids encoding mutant forms of FGF23, as well as the proteins encoded thereby. The invention should be construed to mean all mutations which affect the biological activity or the stability of the FGF23 protein. Preferably, the mutations are associated with hypophosphatemic or hyperphosphatemic conditions, some of which may be heritable, such as, for example, ADHR, as demonstrated by the data presented herein. As documented in the experimental details section herein, several mutant forms of FGF23 render FGF23 more stable than the naturally-occurring wild type form of this protein. Such stable forms of FGF23 are therefore useful as therapeutic compounds for treatment of FGF23 associated disease which is the result of elevated serum phosphate levels. Vectors, including those in which the nucleic acid is operatively linked to promoter/regulatory elements, and cells comprising nucleic acid encoding more stable forms of FGF23 are also contemplated in the invention.

As disclosed herein, mutations in FGF23 have been identified that result in increased stability of the FGF23 protein. Such mutations, including but not limited to R176Q, R179W, and R179Q, have been shown to increase protein stability by eliminating a consensus protease cleavage site, thereby inhibiting protein degradation. The prolonged half-life of these mutant forms of FGF23 is a clear advantage with respect to treating hyperphosphatemic conditions, as the frequency of mutant FGF23 administration necessary for effective treatment maybe significantly less than that of native FGF23. Substitution mutations at either of the arginines at positions 176 and 179 with any amino acid will also increase protein stability. The invention should not be construed to be limited solely to the mutations exemplified herein. In the experimental details section herein, there is provided adequate teaching to enable one of skill in the art to identify additional mutations in the FGF23 gene, wherein the mutant FGF23 may have enhanced stability, etc. when compared with wild type FGF23

The invention provides molecules which are capable of modulating the expression and/or activity of FGF23 in a cell or in a bodily fluid of a mammal.

The mammal is preferably a human.

By the term "modulator" of FGF23 activity, as used herein, is meant a compound that affects the biological activity of FGF23, as defined herein, wherein the activity is either higher or lower in the presence of the modulator compared with the activity of FGF23 in the absence of the modulator.

Thus, a modulator can be an inhibitor or an enhancer of FGF23 expression or activity. Modulators that inhibit FGF23 expression include, but are not limited to, antisense molecules and ribozymes which bind to and/or cleave FGF23 encoding nucleic acid.

The invention provides for inhibitors of FGF23 which serve to reduce or eliminate FGF23 protein molecules. Such inhibitors can be antisense nucleic acids or ribozymes, as described above. Inhibitors can also be double stranded RNA molecules that serve to reduce the level of FGF23 mRNA by RNA interference as described (Elbashir et al., 2001, Nature, 411:428-429; Carthew, 2001, Curr. Opin. Cell Biol., 13:244-248).

The invention further provides for inhibitors of FGF23 which serve to inhibit the biological activity of FGF23, including but not limited to molecules that block the interaction of FGF23 with its receptor or those which inhibit activation of the FGF23 receptor. Specific examples include, but are not limited to, FGFR2, FGFR4 and other FGF23 receptors, and antibodies, peptides, and peptidomimetics that bind to FGF23 or its receptor, thereby inhibiting the biological activity of FGF23. Thus, any type of FGF23 inhibitor is contemplated in the invention, wherein the inhibitor inhibits the expression or biological activity of FGF23.

Based on the sequence of FGF23 disclosed herein, peptidomimetics and other small molecules useful as inhibitors of FGF23 may be generated by the skilled artisan. Specifically, peptidomimetics may be generated using techniques described in PCT/US93/01201.

It is a relatively simple matter, once armed with the present disclosure, to identify a modulator of FGF23 expression or of its biological activity. For example, cells which naturally express FGF23, or which express FGF23 following transfection with FGF23 encoding nucleic acid may be contacted with a test compound. The level of expression of FGF23 in the presence or absence of the test compound is then measured, wherein a higher or lower level of expression of FGF23 in the presence of the test compound compared with the level of FGF23 expression in the absence of the test compound, is an indication that the test compound is a modulator of FGF23 expression. When the level of FGF23 is elevated in the presence of the test compound compared with the level of expression of FGF23 in the absence of the test compound, the test compound is considered to be an enhancer of FGF23 expression. Conversely, when the level of FGF23 expression is reduced in the presence of the test compound compared with the level of expression of FGF23 in the absence of the test compound, the test compound is considered to be an inhibitor of FGF23 expression.

Similarly, FGF23 biological activity can be measured in cells, serum, or urine of a mammal. In this instance, the level of the biological activity of FGF23 produced by cells in the presence or absence of a test compound is measured, wherein a higher or lower level of activity of FGF23 in the presence of the test compound compared with the level of FGF23 activity in the absence of the test compound, is an indication that the test compound is a modulator of FGF23 biological activity. When the level of FGF23 activity is elevated in the presence of the test compound compared with the level of activity of FGF23 in the absence of the test compound, the test compound is considered to be an enhancer of FGF23 biological activity. Conversely, when the level of FGF23 activity is reduced in the presence of the test compound compared with the level of activity of FGF23 in the absence of the test compound, the test compound is considered to be an inhibitor of FGF23 biological activity.

Expression of FGF23 may be measured using any ordinary molecular biology technology, such as using RT-PCR technology, RNAse protection, Northern blotting and the like. Alternatively, affects on expression may be measured by operably linking the FGF23 promoter sequence to a suitable reporter gene and transfecting cells with the resulting DNA construct. Promoter activity responsive to the test compound may be measured by measuring the level of the reporter gene expression in cells contacted with the test compound and comparing the level of reporter gene expression in those cells with cells not contacted with the test compound. Suitable reporter genes include, but are not limited to beta-galactosidase, chloramphenicol acetyl transferase, green fluorescent protein, and the like.

The invention provides for a method of producing an isolated polypeptide having the biological activity of FGF23, as described herein, whereby a host cell comprising a vector encoding FGF23 is cultivated under conditions allowing synthesis of the protein.

The protein is subsequently isolated from the cultivated cells and/or cultivated medium. Isolation and purification of the recombinantly produced proteins may be carried out by conventional means including preparative chromatography and affinity and immunological separations involving affinity chromatography with antibodies which bind specifically with FGF23.

The invention provides for a method of diagnosing hypophosphatemic and hyperphosphatemic disorders in a subject. In one example provided herein, the data establish that patients with ADHR have mutations in FGF23, and FGF23 is useful as a diagnostic tool for detection of ADHR. The method exemplified herein comprises contacting a biological sample obtained from the patient with a reagent which detects FGF23 (or a mutation in FGF23), either a nucleic acid encoding the protein or the protein itself. Detection of FGF23 in the sample, or the absence of detection of FGF23 is diagnostic of FGF23 related hypopohosphatemic and hyperphosphatemic conditions.

The biological sample obtained from the subject may be any fluid or tissue in which FGF23 nucleic acid or protein can be detected. Preferably, the sample is blood or urine. However, the invention should not be construed to be limited to any particular biological sample obtained from the subject.

Preferred reagents for detection of FGF23 nucleic acid include, but are not limited to, a nucleic acid complementary to the nucleic acid encoding FGF23. Preferred reagents for detection of FGF23 protein include, but are not limited to, an antibody. It is further preferred that these reagents be labeled to facilitate detection of FGF23 nucleic acid or protein. One skilled in the art would appreciate, based on the disclosure herein, that regents for detection of FGF23 can be labeled using a variety of suitable labels including a radioisotope, a bioluminescent compound, a chemiluminescent compound, a fluorescent compound, a metal chelate, or an enzyme.

Also included in the invention is a serum, plasma, or other blood assay for hypophosphatemic conditions as well as assays of urine or other bodily fluids. The assay can be used to diagnose patients having the hypophosphatemic diseases listed above. The FGF23 assay is a competitive assay designed to measure a specific peptide corresponding to a portion of FGF23 as well as FGF23. The assay is based upon the competition of labeled $^{125}$I-FGF23 peptide and unlabeled peptide (either standard or an unknown quantity of bodily fluid containing FGF23) binding to the limited quantity of antibodies specific for the FGF23 peptide in each reaction mixture. As the quantity of standard or unknown in the reaction increases, the amount of $^{125}$I-FGF23 peptide able to bind to the peptide in decreased. By measuring the amount of $^{125}$I-FGF23 peptide as a function of the concentration of the unlabeled FGF23 peptide in standard reaction mixtures, a standard curve is constructed from which the concentration of FGF23 in the bodily fluid can be determined.

The competition assay described above is designed to quantitate the level of FGF23 present in a patient's biological sample. By comparing the level of FGF23 polypeptide in a given patient's sample to that of a patient known to be unafflicted by a phosphate disorder, elevated levels of FGF23 can be used as an indication that a given patient is afflicted with a hypophosphatemic disorder. This assay may be useful to many hypophosphatemic disorders, including those for which there is no available genetic means of diagnosis. Hypophosphatemic diseases for which this assay may be useful include XLH, HHRH, HBD, ADHR, tumor induced osteomalacia, epidermal nevus syndrome, fibrous dysplasia, and nephrolithiasis.

For example, as disclosed herein, patients with ADHR will have elevated levels of FGF23 due to mutations in the protein which inhibit its degradation.

The invention also includes a method of diagnosing tumor induced osteomalacia in a patient, wherein the presence of FGF23 in a patient's tumor sample is indicative of this disease, as disclosed herein. A tumor sample excised from a patient can be subject to a variety of methods designed to detect FGF23, including, but not limited to, RT-PCR, Northern blot analysis, and RNase protection assay. Thus, patients which exhibit the clinical symptoms of or induced osteomalacia can be more definitively diagnosed using this FGF23-based procedure.

The invention provides for a method of treating a hypophosphatemic disease in an affected animal, wherein a therapeutically effective amount of a reagent that decreases the expression and/or biological activity of FGF23 is administered to the mammal. Hypophosphatemic diseases which can be treated include, but are not limited to X-linked hypophosphatemic rickets (XLH), hereditary hypophosphatemic rickets with hypercalciuria (HHRH), hypophosphatemic bone disease (HBD), autosomal dominant hypophosphatemic rickets (ADHR), tumor induced osteomalacia (TIO) or oncogenic hypophosphatemic osteomalacia (OHO), epidermal nevus syndrome, fibrous dysplasia, nephrolithiasis, and the like. As disclosed herein, hypophosphatemic disease can be characterized by overexpression of FGF23, mutation or other inhibition of an enzyme that degrades FGF23, or by mutations in FGF23 which increase its protein stability, all of which result in an increase in phosphate wasting accompanied by a decrease in serum phosphate levels. Thus, reagents which decrease the expression and/or biological activity of FGF23 will restore normal phosphate homeostasis in hypophosphatemic patients. Examples of reagents which decrease the expression of FGF23 include, but are not limited to, antisense nucleic acids and ribozymes. Examples of reagents that decrease the biological activity of FGF23 include, but are not limited to, antibodies and other small molecules that block the interaction between FGF23 and its receptor.

The invention also provides for a method of treating hyperphosphatemic disease in a mammal, wherein a therapeutically effective amount of FGF23, either the nucleic acid or the polypeptide encoded thereby, or a reagent that increases the level of FGF23 polypeptide is administered to the mammal. An example of a reagent that increases the level of FGF23 polypeptide is a protease inhibitor. As described in the examples presented herein, FGF23 is degraded by an SPC protease, and inhibition of SPC cleavage of FGF23 prolongs its half life, resulting in higher levels of FGF23. Hyperphosphatemic diseases that can be treated include, but are not limited to patients with mild renal insufficiency, tumoral calcinosis and the like. Elevated levels of serum phosphate in hyperphosphatemic patients can be overcome by administration of FGF23 or a reagent that increases the level of FGF23, both of which stimulate phosphate wasting and thereby reduce serum phosphate levels. FGF23 may be administered by standard gene therapy methods, as well as by direct injection of the FGF23 polypeptide by methods including, but not limited to, intravenous, subcutaneous, and intramuscular injections. The invention should be construed to include administration of native FGF23 as well as mutant forms of FGF23, including, but not limited to, the mutants disclose herein which serve to increase the stability of FGF23 protein.

The invention also included a method of treating a hyperphosphatemic disorder using a therapeutically effective amount of a population of cells expressing FGF23. This method may be an effective method of administering FGF23 since, as shown herein, FGF23 is a secreted protein. Also included in the invention is administration of cells expressing mutant, forms of the FGF2 polypeptide, for this purpose. Preferred mutations include those that confer increased stability upon the FGF23 polypeptide, such as the mutations disclosed herein.

The invention further provides for a method of treating osteoporosis in a mammal, wherein a therapeutically effective amount of FGF23 or a reagent that increases the expression of FGF23 is administered to the mammal. Patients with the hypophosphatemic disease XLH suffer from bone fractures less frequently than patients without the disease (Econs et. al., 1994, Bone and Min., 24:17-24). Administration of FGF23 or a reagent that increases the level of FGF23 would produce transient hypophoshatemia with the accompanying effect on bone density and strength. Thus, in addition to its role in regulation of phosphate homeostasis, FGF23 may have an osteoscleretic function in vivo. While not wishing to be bound by this, the mechanism by which hypophosphatemia leads to increased bone mass likely involves 1,25 dihydroxy vitamin D. Specifically, intermittent administration of FGF23 (or mutant FGF23) or a reagent that increases the expression of FGF23 may transiently decrease phosphate reabsorption, a reaction which stimulates increased phosphate reabsorption and increased production of 1,25 dihydroxy vitamin D, an effective therapeutic agent for a variety of bone diseases.

The invention further provides a method of treating conditions involving deposition of calcium and phosphate in the arteries or soft tissues of a mammal, wherein a therapeutically effective amount of FGF23 (or mutant FGF23) or a reagent that increases the expression of FGF23 is administered to the mammal, as described below. Due to increased serum phosphate levels, patients with mild renal insufficiency commonly exhibit deposition of calcium and phosphorous in their coronary arteries, as well as other arteries. Deposition of both calcium and phosphate in the arterial wall, referred to as coronary artery disease, causes a reduction in blood flow through these arteries and can lead to myocardial infarction. Thus, treatment of coronary artery disease would lessen the risk of developing myocardial infarction.

FGF23 or a reagent that increases the level of FGF23 will reduce the levels of serum phosphate and thereby protect hyperphosphatemic patients from accelerated cardiovascular and coronary artery disease. Nucleic acid encoding FGF23 can be delivered to cells of the coronary artery by methods including, but not limited to, gene therapy. In addition, 20 the use of a tissue-specific promoter can facilitate selective expression of FGF23 in vascular smooth muscle cells or endothelial cells.

Similarly, FGF23 or a reagent that increases the level of FGF23 can be useful in treating other conditions involving deposition of calcium and phosphate in soft tissues, including, but not limited to, dermatomyositis and tumoral calcinosis. Tumoral calcinosis is a disorder characterized by increased renal phosphate reabsorption and increased concentrations of 1,25 dihydrozy vitamin D. As a result patients develop soft tissue calcifications, which are depositions of calcium and phosphate. Administration of FGF23, either native or mutant, to soft tissues using any of the means described herein will reverse the biochemical defects.

The invention includes various kits which comprise a compound, such as a nucleic acid encoding FGF23, an antibody that specifically binds FGF23, a nucleic acid complementary to a nucleic acid encoding FGF23 but in an antisense orientation with respect to transcription, and/or compositions of the invention, an applicator, and instructional materials which describe use of the compound to perform the methods of the invention. Although exemplary kits are described below, the contents of other useful kits will be apparent to the skilled artisan in light of the present disclosure. Each of these kits is included within the invention.

In one aspect, the invention includes a kit for alleviating a disease mediated by malexpression of FGF23. The kit is used pursuant to the methods disclosed in the invention. Briefly, the kit may be used to contact a cell with a nucleic acid complementary to a nucleic acid encoding FGF23 where the nucleic acid is in an antisense orientation with respect to transcription to reduce expression of FGF23, or with an antibody that specifically binds with FGF23, wherein the decreased expression, amount, or activity of FGF23 mediates an beneficial effect. Moreover, the kit comprises an applicator and an instructional material for the use of the kit. These instructions simply embody the examples provided herein.

The kit includes a pharmaceutically-acceptable carrier. The composition is provided in an appropriate amount as set forth elsewhere herein. Further, the route of administration and the frequency of administration are as previously set forth elsewhere herein.

The skilled artisan would appreciate, based upon the disclosure provided herein, that the invention encompasses kits where ribozymes, antisense compositions, antibodies that specifically bind with FGF23 and the like, are included to reduce the level of FGF23.

Further, the invention comprises a kit comprising a nucleic acid encoding a mammalian FGF23. Such a kit can be used according to the methods of the invention wherever increased FGF23 is desired. That is, where a disease, disorder, or condition is associated with or mediated by decreased level of FGF23 compared with normal non-disease level of FGF23, the kit can be used pursuant to the teachings disclosed elsewhere herein, to provide FGF23 to a cell wherein the level of FGF23 in the cell is less than the level of FGF23 in an otherwise identical but normal (i.e., not diseased) cell and/or to an animal comprising such a cell. Mutant forms of FGF23 as disclosed herein, which are more stable than non-mutant forms, are particularly useful in such kits.

Pharmaceutical Compositions

The invention also encompasses the use pharmaceutical compositions of an appropriate FGF23 modulator to practice the methods of the invention, the compositions comprising an appropriate FGF23 modulator and a pharmaceutically-acceptable carrier.

As used herein, the term "pharmaceutically-acceptable carrier" means a chemical composition with which an appropriate FGF23 modulator may be combined and which, following the combination, can be used to administer the appropriate FGF23 modulator to a mammal.

The pharmaceutical compositions useful for practicing the invention may be administered to deliver a dose of between 1 ng/kg/day and 100 mg/kg/day.

Pharmaceutical compositions that are useful in the methods of the invention may be administered systemically in oral solid formulations, aerosol, topical or other similar formulations. In addition to the appropriate FGF23 modulator, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate FGF23 modulator according to the methods of the invention.

Compounds which are identified using any of the methods described herein may be formulated and administered to a mammal for treatment of the diseases disclosed herein are now described.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and other mammals.

Pharmaceutical compositions that are useful in the methods of the invention may be prepared, packaged, or sold in formulations suitable for oral, parenteral, pulmonary, intranasal, buccal, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules composing the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65 degrees F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences*, Mack Publishing Co., Easton, Pa., which is incorporated herein by reference.

Typically dosages of the compound of the invention which may be administered to an animal, preferably a human, range in amount from 1 microgram to about 100 grams per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even lees frequently, such as once every several months or even once a year or less. The frequency of the dose will be readily apparent to the skilled artisan and will depend upon any number of factors, such as, but not limited to, the type and severity of the disease being treated, the type and age of the animal, etc.

Deposit. Under the terms of the Budapest Treaty on the International Recognition of the Deposit of Microorganisms for the Purpose of patent Procedure, deposit of nucleic acid including FGF23 DNA, was made with the German Collection of Microorganisms and Cell Cultures (DSMZ) on Jun. 14, 2000, as Deposit No. DSM 13530.

The nucleotide sequence of the deposited clone can readily be determined by sequencing the deposited clone in accordance with known methods. The amino acid sequence can then be verified from such deposit. Moreover, the amino acid sequence of the protein encoded by the deposited clone can also be directly determined by peptide sequencing or by expressing the protein in a suitable host cell containing the deposited FGF23-encoding DNA, collecting the protein, and determining its sequence.

Applicant's assignees, Advanced Research and Technology Institute and LMU Munchen, represents that the DSMZ is a depository afforded permanence of the deposit and ready accessibility thereto by the public if a patent is granted. All restrictions on the availability to the public of the material so deposited will be irrevocably removed upon granting of a patent. The material will be readily available during the pendency of the patent application to one determined by the Commissioner to be entitled thereto under 37 C.F.R. §1.14 and 35 U.S.C. §122. The deposited material will be maintained with all the care necessary to keep it viable and uncontaminated for a period of at least five years after the most recent request for the furnishing of a sample of the deposited material, and in any case, for a period of at least thirty (30) years after the date of the deposit or for the enforceable life of the patent, whichever period is longer. Applicant's assignee acknowledges its duty to replace the deposit should the depository be unable to furnish a sample when requested due to the condition of the deposit.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, the phrase "allelic variant" refers to a nucleotide sequence which occurs at a given locus or to a polypeptide encoded by the nucleotide sequence.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |

-continued

| Full Name | Three-Letter Code | One-Letter Code |
|---|---|---|
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, to "alleviate" a disease, disorder or condition mediated by or associated FGF23.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

By the term "applicator" as the term is used herein, is meant any device including, but not limited to, a hypodermic syringe, a pipette, a nebulizer, and the like, for administering the a nucleic acid, protein, and/or composition of the invention to a mammal.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

By "complementary to a portion or all of the nucleic acid encoding FGF23" is meant a sequence of nucleic acid which does not encode FGF23 protein. Rather, the sequence which is identical to the non-coding strand of the nucleic acid encoding FGF23 and thus, does not encode FGF23 protein.

The terms "complementary" and "antisense" as used herein, are not entirely synonymous. "Antisense" refers particularly to the nucleic acid sequence of the non-coding strand of a double stranded DNA molecule encoding a protein, or to a sequence which is substantially homologous to the non-coding strand. "Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

"Homologous" refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGCG5' share 50% homology.

A first oligonucleotide anneals with a second oligonucleotide with "high stringency" if the two oligonucleotides anneal under conditions whereby only oligonucleotides which are at least about 60%, more preferably at least about 65%, even more preferably at least about 70%, yet more preferably at least about 80%, and preferably at least about 90% or, more preferably, at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, *Molecular Cloning: A Laboratory Manual*, Cold Spring Harbor Laboratory, N.Y.).

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example, at the National Center for Biotechnology Information (NCBI) world wide web site having the universal resource locator www<dot>ncbi<dot>nlm<dot>nih<dot>gov/BLAST/. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used. See www<dot>ncbi<dot>nlm<dot>nih<dot>gov.

The percent identity between two sequences can be determined using techniques similar to those described above, with or without allowing gaps. In calculating percent identity, typically exact matches are counted.

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

As used herein, the term "fragment" as applied to a nucleic acid, may ordinarily be at least about 10 nucleotides in length, typically, at least about 20 nucleotides, more typically, from about 20 to about 50 nucleotides, preferably at least about 50 to about 100 nucleotides, even more preferably at least about 100 nucleotides to about 500 nucleotides, yet even more preferably at least about 500 to about 1,000, and most preferably, the nucleic acid fragment will be greater than about 1,500 nucleotides in length.

As used herein, the term "fragment" as applied to a polypeptide, may ordinarily be at least about seven contiguous amino acids, typically, at least about fifteen contiguous amino acids, more typically, at least about thirty contiguous amino acids, typically at least about forty contiguous amino acids, preferably at least about fifty amino acids, even more preferably at least about sixty amino acids and most preferably, the peptide fragment will be greater than about seventy contiguous amino acids in length.

As used herein, the term "hybridizes under stringent conditions" is intended to describe conditions for hybridization and washing under which nucleotide sequences at least 60% (65%, 70%, preferably 75%) identical to each other typically remain hybridized with each other. Such stringent conditions are known to those skilled in the art and can be found in In: Current Protocols in Molecular Biology, at 6.3.1-6.3.6, John Wiley & Sons, N.Y. (1989). An example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to the sequence of any of SEQ ID NOs: 1 or 3, or a complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

A "genomic DNA" is a DNA strand which has a nucleotide sequence homologous with a gene. By way of example, both a fragment of a chromosome and a cDNA derived by reverse transcription of a mammalian mRNA are genomic DNAs.

As used herein, "homology" is used synonymously with "identity."

In addition, when the term "homology" is used herein to refer to the nucleic acids and proteins, it should be construed to be applied to homology at both the nucleic acid and the amino acid levels.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

"Derivatives," and "variants" of the peptides of the invention (or of the DNA encoding the same) are peptides which may be altered in one or more amino acids (or in one or more base pairs) such that the peptide (or DNA) is not identical to the sequences recited herein, but has the same property as the peptides disclosed herein, in that the peptide has biological activity of FGF23.

The term "mutation in a nucleic acid encoding FGF23" means any base pair change in the nucleic acid sequence whether it changes the protein's structure or function or has no effect. Some mutations, including, but not limited to, R176Q, R179Q, R179W and any other mutation in either of these two arginines, affect protein stability and, therefore, may affect half life in the blood or other biological effects.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

The term "expression of a nucleic acid" as used herein means the synthesis of the protein product encoded by the nucleic acid.

The use of the term "DNA encoding" should be construed to include the DNA sequence which encodes the desired protein and any necessary 5' or 3' untranslated regions accompanying the actual coding sequence.

By the term "positioned at the 5' end" as used herein, is meant that the promoter/regulatory sequence is covalently bound to the 5' end of the nucleic acid whose expression it regulates, at a position sufficiently close to the 5' start site of transcription of the nucleic acid so as to drive expression thereof.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences"

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, Methods for General and Molecular Bacteriology, American Society for Microbiology, Washington, D.C., p. 574).

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A "restriction site" is a portion of a double-stranded nucleic acid which is recognized by a restriction endonuclease.

A portion of a double-stranded nucleic acid is "recognized" by a restriction endonuclease if the endonuclease is capable of cleaving both strands of the nucleic acid at the portion when the nucleic acid and the endonuclease are contacted.

By the term "specifically binds," as used herein, is meant a compound, e.g., a protein, a nucleic acid, an antibody, and the like, which recognizes and binds with a specific molecule, but does not substantially recognize or bind other molecules in a sample.

A first oligonucleotide anneals with a second oligonucleotide "with high stringency" if the two oligonucleotides anneal under conditions whereby only oligonucleotides which are at least about 60%, preferably at least about 65%, more preferably at least about 70%, even more preferably at least about 75%, and preferably at least about 90% or at least about 95%, complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, Molecular Cloning: A Laboratory Manual, Cold Spring Harbor Laboratory, New York).

As used herein, the term "substantially pure" describes a compound, e.g., a nucleic acid, protein or polypeptide, which has been separated from components which naturally accompany it. Typically, a compound is substantially pure when at least about 10%, preferably at least about 20%, more preferably at least about 50%, still more preferably at least about 75%, even more preferably at least about 90%, and most preferably at least about 99% of the total material (by volume, by wet or dry weight, or by mole percent or mole fraction) in a sample is the compound of interest. Purity can be measured by any appropriate method, e.g., by column chromatography, gel electrophoresis or HPLC analysis.

A compound, e.g., a nucleic acid, a protein or polypeptide is also "substantially purified" when it is essentially free of naturally associated components or when it is separated from the native contaminants which accompany it in its natural state. Thus, a "substantially pure" preparation of a nucleic acid, as used herein, refers to a nucleic acid sequence which has been purified from the sequences which flank it in a naturally occurring state, e.g., a DNA fragment which has been removed from the sequences which are normally adjacent to the fragment in a genome in which it naturally occurs.

Similarly, a "substantially pure" preparation of a protein or a polypeptide, as used herein, refers to a protein or polypeptide which has been purified from components with which it is normally associated in its naturally occurring state. A substantially pure peptide can be purified by following known procedures for protein purification, wherein an immunological, enzymatic or other assay is used to monitor purification at each stage in the procedure. Protein purification methods are well known in the art, and are described, for example in Deutscher et al. (1990, In: *Guide to Protein Purification*, Harcourt Brace Jovanovich, San Diego).

By "tag" polypeptide is meant any protein which, when linked by a peptide bond to a protein of interest, may be used to localize the protein, to purify it from a cell extract, to immobilize it for use in binding assays, or to otherwise study its biological properties and/or function. A chimeric (i.e., fusion) protein containing a "tag" epitope can be immobilized on a resin which binds the tag. Such tag epitopes and resins which specifically bind them are well known in the art and include, for example, tag epitopes comprising a plurality of sequential histidine residues (His6), which allows isolation of a chimeric protein comprising such an epitope on nickel-nitrilotriacetic acid-agarose, a hemagglutinin (HA) tag epitope allowing a chimeric protein comprising such an epitope to bind with an anti-HA-monoclonal antibody affinity matrix, a myc tag epitope allowing a chimeric protein comprising such an epitope to bind with an anti-myc-monoclonal antibody affinity matrix, a glutathione-S-transferase tag epitope, and a maltose binding protein (MBP) tag epitope, which can induce binding between a protein comprising such an epitope and a glutathione- or maltose-Sepharose column, respectively. Production of proteins comprising such tag epitopes is well known in the art and is described in standard treatises such as Sambrook et al., 1989, and Ausubel et al., supra. Likewise, antibodies to the tag epitope (e.g., anti-HA, anti-myc antibody 9E10, and the like) allow detection and localization of the fusion protein in, for example, Western blots, ELISA assays, and immunostaining of cells.

As used herein, to "treat" means reducing the frequency with which symptoms are experienced by a patient.

As used herein, an "inhibitor of FGF23" is defined as any molecule that serves to reduce or eliminate FGF23 protein molecules or their biological activity. Such inhibitors can be antisense nucleic acids or ribozymes, molecules that block the interaction of FGF23 with its receptor or those which inhibit activation of the FGF23 receptor. Specific examples are discussed above.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector which is suitable as a delivery vehicle for delivery of the nucleic acid encoding the desired protein, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Linkage and Mutational Analysis of ADHR Families

The data herein demonstrate the discovery of a novel gene, FGF23. Also demonstrated below is the discovery that ADHR maps to the short arm of chromosome 12 into 12p13.3, FGF23 maps into this region, and FGF23 is mutated in individuals suffering from ADHR.

The materials and methods used in the experiments presented in this example are now described.

Pedigree Analysis

Pedigrees of families of British (family 2318), German (family 329), and American (families 1406 and 1478) origin were analyzed. The ADHR+ families 1406, 1478 and 2318 have been described previously (Econs, et al. 1992, J. Clin. Endocrinol. Metab. 82:674-681; Bainchine, et al. 1971, Birth Defects Orig. Aric. Ser. 7:287-295; Rowe, et al. 1992, Hum. Genet. 89:539-542). The study was approved by the Indiana University School of Medicine and the Ludwig-Maximilians-Universitat Faculty of Medicine Institutional Review Boards, and all patients gave informed consent before participating.

Mutation Screening

Patient DNA was evaluated as follows: Exons were amplified with intronic primers (Table 2) and amplified fragments were analyzed either by direct sequencing or SSCP. SSCP were performed using standard polyacrylamide or Serdogel SSCP 2x (Serva Electrophoresis GmbH, Heidelberg, Germany) at 20° C. with and without glycerol. Samples were visualized either by staining with Tt4cslistraGreen and detection with a FluorImager (Molecular Dynamics, Sunnyvale, Calif.) or by autoradiography after PCR amplification of exons in the presence of [$^{32}$P]dCTP. Variant bands were reamplified for sequencing. Direct sequencing with both the sense and antisense primer was performed either using a Taq DyeDeoxy Terminator Cycle sequencing kit (ABI) or using a Sequenase Kit (USB) and incorporation of [$^{33}$P] dideoxy-nucleotides. Mutational analysis was performed using DNA from index patients of 4 families, 1406, 1478, 2318 and 329, that had male to male transmission and clinical features compatible with ADHR, as well as DNA from 18 patients with hypophosphatemic rickets that were negative for PHEX gene mutations. Furthermore, a family with hypophosphatemia, major craniofacial abnormalities and short upper and lower extremities (Cabral, et al., 80$^{th}$ Annual Endocrine Society Meeting 1998) as well as a family with HBD that contained a male to male transmission were analyzed.

RT-PCR/RACE

RT-PCR was performed using 1-2 ng of human or mouse FGF23 cDNA (FIG. 5 or 6) as templates. RACE was done using the Marathon cDNA Amplification Kits (ClonTech Inc. Palo Alto, Calif.). Primers designed from the predicted cDNA sequences were used for amplification of 0.2-3.5 kb products (Table 2) and are available on request. Human fetal chondrocyte cell cultures were prepared as described by Bonaventure, et al. 1994, Exp. Cell Res 212:97-104, and checked for the expression of COL2A1.

The results presented in this example are now described.

Figure 2:
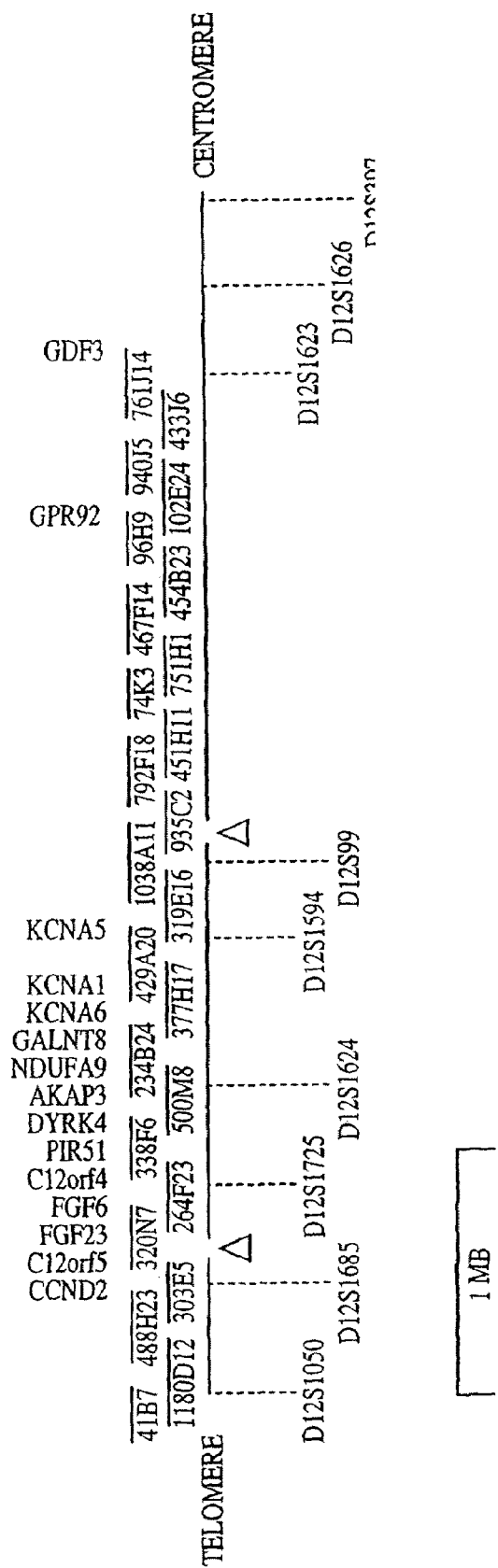
FIG. 2 is a diagram depicting a physical map of the ADHR region. The position of DNA markers and BACs/PACs are drawn to scale as estimated by the unfinished sequence data (Baylor College of Medicine Human Genome Sequencing Center). Arrows indicate gaps in the genomic sequence between clone RP11-303E5 and RP11-320N7, and clone RP11-103A11 and RP11-935C2. The approximate positions of genes between D12S1624 and D12S1594 and of GPR46 and GDF2 are indicated.

Linkage analysis in a large ADHR pedigree, family 1406, demonstrated significant LOD scores for an 18 cM interval on chromosome 12p13.3 between markers D12S100 and D12S397. Two point LOD score for marker D12S1624 was 7.68. A second, smaller ADHR kindred, family 1478, displayed a LOD score of 1.1 at D12S1624. Assuming that the disease locus in this family was linked to the same interval, it was screened for single recombination events in these two families and mapped the disease locus to the 1.5 MB region between the markers D12S1685 and S12S1594 (FIG. 2). In family 1406, individuals 1306 and 0142 had proximal recombination events at D12S1685 and distal recombination evens at D12S397. Family 1478 exhibited recombination at D12S1050 and D12S1594 in individuals 001 and 0100, respectively (FIG. 1A).

Genomic sequences from 12p13.3 are available from the public human genome effort. An annotation of finished and unfinished sequences between D12S685 and D12S1623 revealed 37 genes within this region, 13 of which are novel. The complete coding sequences of the novel genes were obtained by RT-PCR, RACE and/or sequencing of IMAGE clones.

Based upon the above linkage studies, the mutation screen was concentrated on the 1.5 MB region between D12S1685 and D12S1594. This region contains 7 known, 4 novel genes, and 1 gene fragment (Table 1). The following genes were screened for mutations by amplification of exons with primers based on exon-intron boundaries: (i) MIBOO3 (AJ272206): (ii) DYRK4 protein kinase (AF263541); (iii) Protein kinase A binding protein AKAP11O (AF093408); (iv) GalNAc-T8 (AJ271385)9. In addition, several genes outside of this region were considered candidates. Two of them, growth differentiation factor 3 (GDF3, AF263538), as well as a novel G-protein coupled receptor (GPCR46, AJ272207) were investigated. Few variations were detected and sequencing of control alleles revealed all of them to be polymorphisms (Table 1).

TABLE 1

| Acc No: | Gene symbol | ORF(aa) | Exons | pter-qter | Polymorphisms |
|---|---|---|---|---|---|
| M90813 | CCND2 | 289 | | | |
| AJ272206* | C12orf5 | 270 | 6 | forward | 716C/T(T293M) |
| AF263537 | FGF23 | 251 | 3 | reverse | |
| X63454 | FGF6 | 198 | 3 | reverse | |
| M272205 | C12orf4 | 552 | 14 | reverse | |
| AF006259 | PIR51 | 335 | 9 | forward | |
| AF263541* | DYRK4 | >541 | >11 | forward | 351C/T(V117V) 632A/G(N211 S) 1041 C/T(A347A) |
| AF093408* | AKAP3 | 853 | 5 | reverse | |
| AF050641 | NDUFA9 | 377 | 11 | forward | |
| AJ271385* | GALNT8 | 637 | 11 | forward | 800A/G(E267G) |
| X17622 | KCNA6 | 529 | 1 | forward | |
| L02750 | KCNAI | 495 | 1 | forward | |

A novel fibroblast growth factor family member from this region, FGF23, was also investigated. Direct sequencing of FGF23 exons from the above ADHR families revealed three missense changes affecting two arginines, which lie three amino acids apart. Families 1406 and 1478 shared the same change, R176Q (527>A), which disrupts an AciI site. The control PCR product was digested into fragments of 112, 49, and 33 bp, whereas the mutant alleles only produced 112 and 82 bp fragments when analyzed by agarose gel electrophoresis. In family 2318, a R179W (535C>T) change in mutant FGF23 was found which creates a new BmpI site. RFLP analysis showed that the PCR product from the normal allele was not digested, leaving the original product of 194 bp, whereas the mutant alleles were cut a single time resulting in 118 and 87 bp fragments (FIG. 1B). In family 329, a R179Q (536G>A) change in mutant FGF23 was found which dies not create or destroy a restriction site. Furthermore, a polymorphism was present in exon 3, 716/T (239/M). Threonine was found in 182 out of 214 alleles, and methionine was found in 22 out of 214 alleles. Sequencing of the entire coding region and of the region upstream of the initiation codon (450 bp) revealed no mutations in the family with HBD, the family with hypophosphatemia and multiple congenital abnormalities, as well as in the eighteen patients with XLH. The missense mutations segregated with the disease in each family and are not found in 214 sequenced control alleles. In addition, the mutation in families 1406 and 1478, and in family 2318 were excluded by RFLP analysis in 800 and 752 control alleles, respectively (FIG. 1B). Kindreds 1406 and 1478, who had identical FGF23 mutations, are from separate geographical regions and are not known to be related. In support of this, the two families have different alleles at D12S1624 and D12S1725, loci only 200 kb and 70 kb distant from the mutant gene, respectively. In summary, it is apparent that the FGF23 mutations R176Q, R179Q and R179W are causative for ADHR.

Figure 3A:
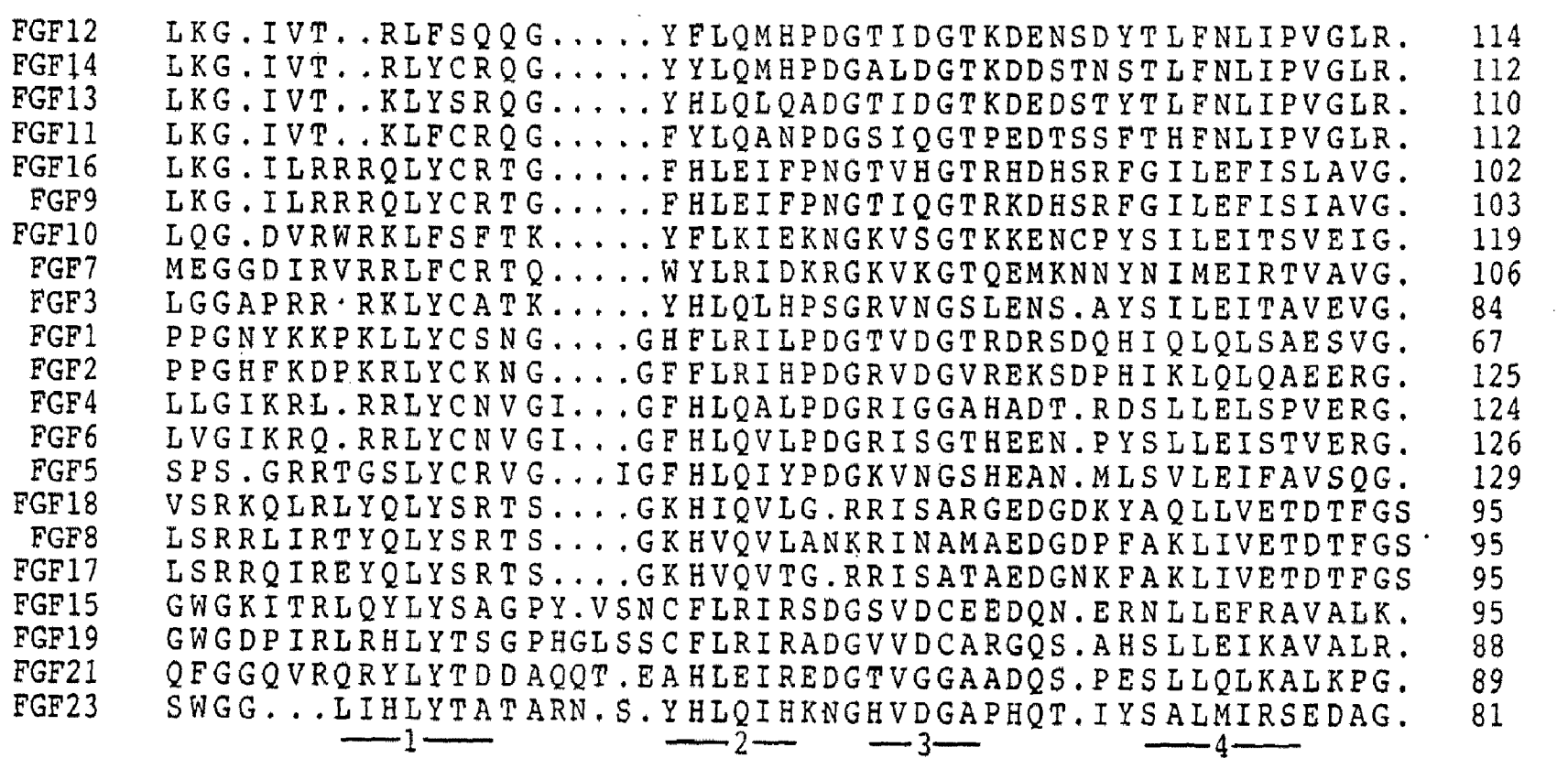
Figure 3C:
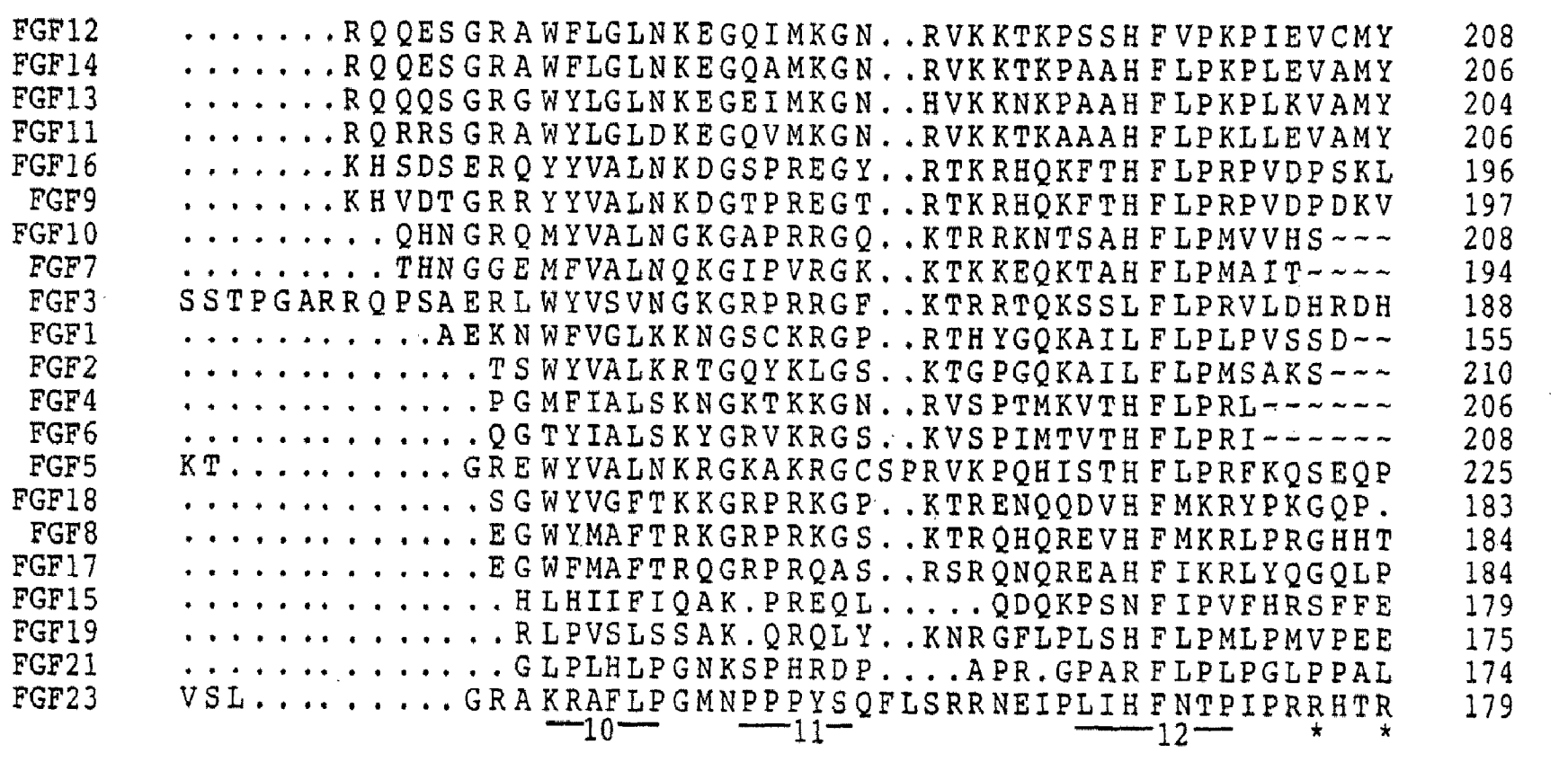

FGF23 lies 54 kb telomeric of FGF-6 in the human genome and is comprised of three exons, spanning approximately 10 kb of genomic sequence. The longest FGF23 RT-PCR product obtained is 1612 bp and contains a predicted open reading frame (ORF) of 251 amino acids. The 5'-UTR consists of 146 bp with no in-frame stop codon present upstream of the predicted start site. The 3'-UTR consisted of 710 bp with a polyadenylation signal predicted 831 bp downstream of the stop codon. Human and mouse FGF23 were identified by the FGF profile of the PFAM database (4.6e-14, 1.9e-16). An amino acid sequence alignment was generated between FGF23 and other members of the FGF family using CLUSTAL and PRETTYBOX (FIG. 3A-3C). They share 25% to 36% amino acid identity with the other members of the FGF family in the common core sequence. Tree analysis indicates that FGF23 is most closely related to FGF-21. Given the fact that FGF23 has 251 amino acids, it is, to date, the largest FGF as characterized by a large C-terminal part of the protein. Analysis with Signal P indicated that FGF23 contains a signal peptide and cleavage of the peptide most likely between the alanine residue at position 24 and the tyrosine at position 25.

BACs from mouse chromosome 6 were sequenced within the homologous region to human chromosome 12p13.3. One of these BACs (GenBank accession number ACO15538) contained the mouse homolog of FGF23. Primers derived from the corresponding region were used to amplify FGF23 from day 17 mouse embryo cDNA. The murine cDNA has a predicted ORF of the same length as the human protein, with 73% identity at the nucleotide level and 70% identity on the amino acid level. Furthermore, dot plot analysis indicated substantial sequence conservation between the mouse and human sequence 500 bp upstream of the initiation codon.

Example 2

Expression of FGF23

The data herein demonstrate expression of FGF23 in human tissues and cancer cell lines. Also demonstrated in this example is generation of an antibody specific for FGF23 and its use to detect FGF23 produced in bacterial and mammalian cells. The data presented in this example further demonstrate that FGF23 is a secreted protein and that FGF23 is expressed abundantly in oncogenic hypophosphatemic osteomalacia (OHO) tumors.

The materials and methods used in the experiments presented in this example are now described.

Northern Blot Analysis.

Multiple tissue Northern blots containing 2 pg polyA$^+$-RNA from each tissue (ClonTech Inc. Palo Alto, Calif.) were incubated with full length FGF23 (FIG. 5A or 6A) probe in hybridization buffer (270 mM NaCl, 15 mM Na2HPO4, 15 mM EDTA, 1% SDS, 10% Dextran sulfate 0.5% skimmed milk powder) at 65° C. with washing in 0.01×SSC at 60° C.

Bacterial Production of FGF23.

A human FGF23 cDNA was produced by PCR amplification of RNA from human heart (ClonTech Inc. Palo Alto, Calif.) using Pfu polymerase (Gibco-BRL, Rockville, Md.). An insert comprising nucleotides 73-756, that encodes the full-length FGF23 without the predicted signal peptide, was directionally cloned into the pQE30 vector in frame with an N-terminal 6×His tag using the Type IV Qiaexpress Kit (Qiagen, Inc., Valencia, Calif.). The plasmid, FGF23-6×His pQE, was subsequently used for transformation of M15 [pREP4] cells and IPTG was added for four hours to induce protein expression. FGF23-6×His protein was purified by nickel chromatography minipreps as described by the manufacturer (Qiagen Inc., Valencia, Calif.).

Western Blot Analysis.

Protein samples and standards were electrophoresed on 15% SDS-PAGE mini-gels (BioRad) and electroblotted onto nitrocellulose membranes. Membranes were incubated with 2.5 µg/ml anti-human FGF23 antibody or mouse anti-penta-His antibody, and subsequently with goat anti-rabbit or anti-mouse-HRP secondary antibody (1:1000) (Amersham, Inc., Piscataway, N.J.), and visualized by enhanced chemiluminescence (ECL) (Amersham, Inc., Piscataway, N.J.).

Production of FGF23 in Mammalian Cells.

To produce FGF23 in mammalian cells, OK-E, COS-7, and HEK293 cells were transiently transfected with a plasmid expressing human FGF23, designated pFGF23. To construct pFGF23, the FGF23 ORF preceded by the Kozak sequence (bp −3 to 756) was amplified by RT-PCR from heart total RNA. The resulting cDNA was directionally inserted into the expression plasmid pcDNA3.1 (+) (Invitrogen). The integrity of pFGF23 was confirmed by DNA sequencing.

Preparation of OHO Tumor Samples.

Figure 8A:
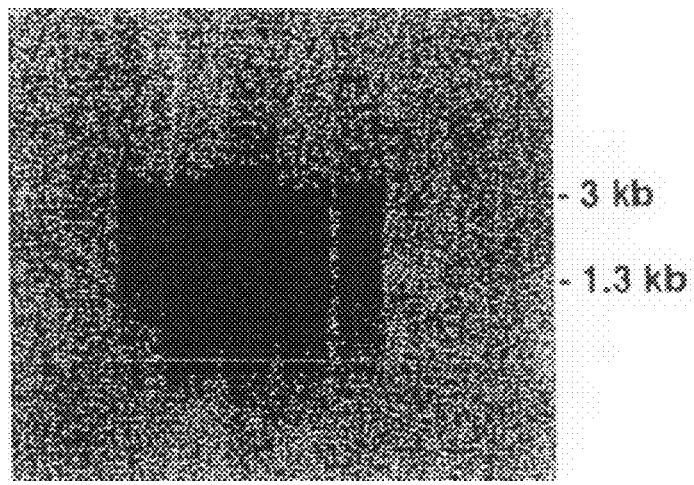
FIG. 8A is an image of a Northern blot depicting expression of FGF23 in oncogenic hypophosphatemic osteomalacia (OHO) tumors. Northern blot analysis of total RNA from five different OHO tumors (lanes 3-7) displayed strongly-hybridizing FGF23 transcripts of 1.3 and 3 kb and a faint 2 kb band after a 30-minute exposure, whereas control tissues were negative. (Lane 1=human liver; lane 2=human parathyroid, lane 8=mouse brain; lane 9=mouse heart; lane 10=mouse kidney.)

Six different tumors from OHO patients were obtained by surgical removal from: a) left thigh (hemangiopericytoma); b) mandible (mixed connective tissue tumor); c) left thigh (angiodysplasia); d) sole of foot (hemangiopericytoma); e) nose (hemangiopericytoma); and f) distal femur (osteoblastic osteosarcoma) (FIG. 8A). All patients exhibited biochemical abnormalities characteristic of OHO, which resolved after tumor removal. Approximately 100 mg of tumor sample was resuspended in 0.5 ml of ice cold phosphate-buffered saline (PBS) supplemented with 75 µg/ml AEBSF protease inhibitor. The sample was homogenized for 30 seconds on ice, then centrifuged at 1500 g and then the cleared homogenate was used for further experiments. Protein concentrations were determined by Bradford protein assay (Bio-Rad, Inc., Hercules, Calif.) with bovine serum albumin as the standard.

The results of the experiments presented in this section are now described.

Figure 4A:
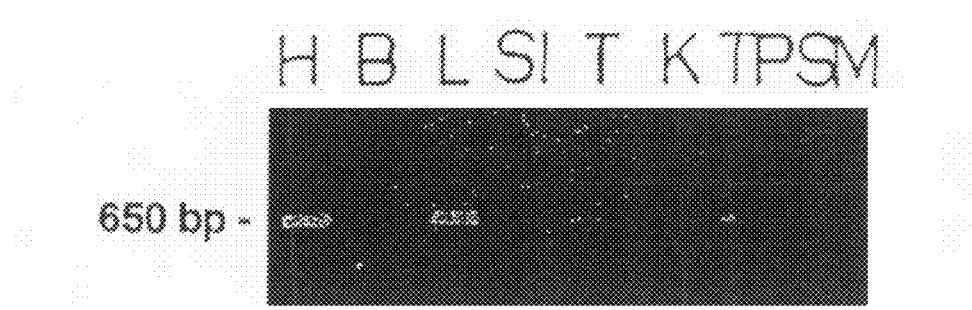
FIG. 4A is an image of an agarose gel depicting tissue expression of FGF23. RT-PCR analysis of RNA from human tissues using intron-spanning primers revealed a 650 bp product in human heart (H), liver (L), thyroid/parathyroid (TP), small intestine (SI), testis (T), and skeletal muscle (SM), whereas brain (B) and kidney (K) were negative.
Figure 4B:
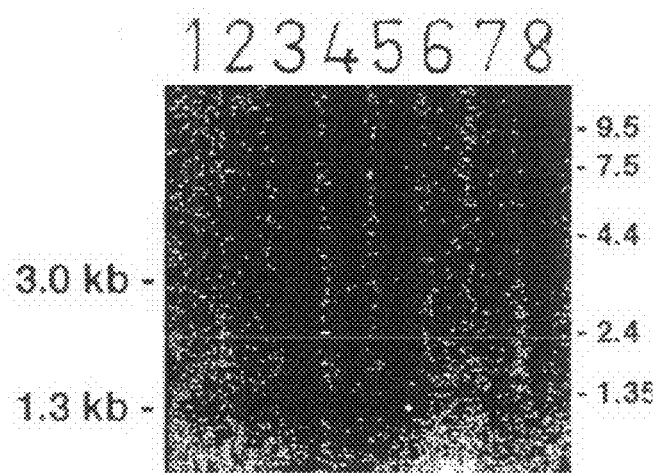
FIG. 4B is an image of a Northern blot depicting FGF23 expression in multiple cancer cell lines after a 7 day exposure. Transcripts of 3 and 1.3 kb were observed under stringent washing conditions in the chronic mylogenous leukemia cell line K562 (lane 3). Other cell lines produced either the 3 or 1.3 kb transcript. (Lane 1=HL-60; lane 2=HeLaS3; lane 4=MOLT-4; lane 5=RAJI; lane 6=SW480; lane 7=A549; lane 8=G-361.)

To evaluate expression of FGF23 in specific human tissues as well as in cancer cell lines, RT-PCR and hybridization analysis of RNA obtained from human tissues and cancer cell lines was carried out according to conventional methods. It was shown that FGF23 was transcribed at low levels in specific tissues, such as human heart, liver, and thyroid/parathyroid (FIG. 4A). Furthermore, fainter products could be amplified from whole fetus, fetal condrocytes, small intestine, testis and skeletal muscle. Lung, brain, kidney, osteosarcoma cells (SaOS), and endothelial cells (HMEC-1) were negative for FGF23 transcript. In mice, nested RT-PCR was positive in day 17 mouse embryos, but not in primary bone cell cultures from calvaria, limb bud cells, osteoblasts (MC3T3 cells), and a stimulated chondrocyte cell line. Radioactive in situ hybridization on sagittal sections of mouse embryos at different developmental stages, as well as on paraffin sections of various tissues, such as adult lung, ovary, pancreas, testis, thymus, kidney, brain, and heart and frozen sections of E18.5 tibias were negative for FGF23 transcript. Hybridization of multiple tissue Northern blots from sixteen specific organs was negative. Northern blot analysis of RNA obtained from cancer cell lines displayed a positive signal of approximately 3 and 1.3 kb in the chronic myelogenous leukemia cell line K562 when probed with the FGF23 cDNA, whereas several other tumor cell lines expressed only the 3.0 or the 1.3 kb transcript (FIG. 4B).

To generate an immunological reagent useful for detection of FGF23, rabbit anti-human FGF23 polyclonal antibodies were produced using standard protocols against the peptide CSQELPSAEDNSPMASD-COOH (SEQ ID NO:5), which corresponds to residues 206-222 of human FGF23 (Zymed Laboratories, Inc., South San Francisco, Calif.). The antiserum was affinity purified against the peptide.

To assess the specificity of the anti-FGF23 antibody, recombinant human FGF23 was produced in bacteria as described above. Lysates prepared from FGF23-6×His pQ-transformed bacteria were analyzed by Western blot analysis using the affinity-purified anti-FGF23 antibody. Anti-FGF23 antibody recognized a protein of approximately 27 kDa from IPTG-induced bacteria, whereas no protein was detected in uninduced cultures (FIG. 7A). The same protein was also detected with an anti-His antibody, indicating that both antibodies recognized identical proteins. Pre-immune sera failed to detect a protein in all experiments. These results confirm that the affinity-purified anti-FGF23 antibody recognized recombinant human FGF23 protein.

To evaluate expression of FGF23 in transfected cells, cells were harvested at 24 hours post transfection, total RNA was extracted, and Northern blot analysis was performed using a $^{32}$P-labeled FGF23 cDNA probe. In all three cell lines transfected with pFGF23, a single mRNA species of 1.1 kb hybridized to the FGF23 probe, whereas cells transfected with empty pcDNA3.1 did not express an FGF23 transcript (FIG. 7B).

To determine if FGF23 is a secreted protein, Western blot analysis was performed using conditioned media derived from the three transfected cell lines and the anti-FGF23 antibody. Immunoreactive proteins of approximately 32 kDa and 12 kDa were detected in the conditioned media obtained from the pFGF23-1-transfected cells, but not from pcDNA3.1-transfected cells (FIG. 7C). The 32 kDa band was the mature form of FGF23, and the 12 kDa species represents a C-terminal degradation product of FGF23 because the smaller band was only detected after extended incubation of the cells in serum-free media. In addition, the secreted form of FGF23 was larger than its predicted size most likely due to core glycosylation, as tested by in vitro transcription and translation of pFGF23 in the presence of pancreatic microsomes. Taken together, these results demonstrate that mammalian cells transiently expressing FGF23 can generate an FGF23 transcript and efficiently secrete the protein.

Figure 8B:
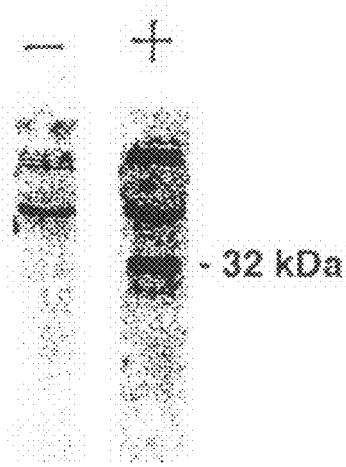
FIG. 8B is an image of a Western blot depicting FGF23 protein expression in an OHO tumor sample. Analysis of two micrograms of extract from an OHO tumor demonstrated that a protein of 32 kDa was detected by anti-FGF23 antibody (+), but not by pre-immune sera (−).

To assess FGF23 expression in OHO tumors, Northern blot analysis was performed using total RNA isolated from five of the six tumors. Radiolabeled FGF23 probe hybridized with FGF23 transcripts of 3.0 and 1.3 kb, as well as a faint band at approximately 2.0 kb in all five tumors; in contrast, the control RNAs from several other tissues demonstrated no hybridizing bands (FIG. 8A). To determine whether FGF23 protein is present in OHO tumors, extracts from a sixth tumor were examined by Western blot analysis using the anti-FGF23 antibody. The FGF23 antibody detected a protein of 32 kDa from tumor extracts (FIG. 8B). In summary, Northern and Western blot analysis indicate that FGF23 is a secreted protein which is highly expressed in OHO tumors.

Example 3

The Effects of ADHR Mutations on FGF23 Protein Cleavage and Heparin Binding

The data herein demonstrate that FGF23 mutations that are linked to ADHR results in increased levels of the larger protein species of FGF23, due to an inability of proteases to efficiently cleave FGF23 at a consensus SPC site. Also demonstrated in this example is the ability of mutant forms of FGF23 to bind heparin at levels comparable to wild-type FGF23.

The materials and methods used in the experiments presented in this example are now described.

Mutagenesis of FGF23.

The ADHR missense mutations, R176Q, R179W, R179Q, were introduced into the FGF23 cDNA using a nested PCR, site-directed mutagenesis approach. The high-fidelity DNA polymerase Pfu (Promega, Inc., Madison, Wis.) was used in all PCR reactions using pFGF23 (pcDNA3.1 backbone) as a template. For the initial round of PCR, each forward mutagenic primer containing the appropriate missense was paired with the reverse 3'FGF23 primer and each reverse mutagenic primer was paired with the forward 5'FGF23 primer. Mutagenic primers are listed below in Table 2. The BamHI and EcoRI sites located within in the 5'FGF23 and 3'FGF23 primers, respectively, are italicized and double underlined. The mutated base within each primer is underlined.

TABLE 2

| Primer Name/SEQ ID NO: | Primer orientation | Sequence (5'-3') |
|---|---|---|
| 5'FGF23 Primer (SEQ ID NO: 6) | Forward | CG*GGATCC*ACGATGTTGGGGGCCCG |
| 3'FGF23 Primer (SEQ ID NO: 7) | Reverse | G*GAATTC*CTAGATGAACTTGGCGAA |
| R176Q (G527A) (SEQ ID NO: 8) | Forward | ATACCACGGCAGCACACCCGG |
| R176Q (G527A) (SEQ ID NO: 9) | Reverse | CCGGGTGTGCTGCCGTGGTAT |
| R179W (C535T) (SEQ ID NO: 10) | Forward | GCGGCACACCTGGAGCGCCGA |
| R179W (C535T) (SEQ ID NO: 11) | Reverse | TCGGCGCTCCAGGTGTGCCGC |
| R179Q (G536A) (SEQ ID NO: 12) | Forward | CGGCACACCCAGAGCGCCGAG |
| R179W (G536A) (SEQ ID NO: 13) | Reverse | CTCGGCGCTCTGGGTGTGCCG |

PCR conditions for all experiments were: 1 minute 95° C., followed by 35 cycles of 1 minute 95° C., 1 minute 55° C., 2 minutes 72° C., and a final extension of 7 minutes at 72° C. The resulting cDNA products from the first round of PCR were gel purified using the Wizard Prep Kit (Promega Corp., Madison, Wis.). The second round of PCR was used to produce full-length mutant cDNAs. One μl from each of the two initial PCR reactions for a specific mutant was combined into a single reaction tube and this mixture of two cDNAs was amplified with the 5'FGF23 and 3'FGF23 primers. The resulting products were then digested with BamHI and EcoRI and directionally ligated into the expression plasmid pcDNA3.1 (+) to create mutant clones pR176Q, pR179W, pR179Q. Each mutant clone insert was sequenced to confirm that the appropriate mutations were introduced, as well as to assure integrity of the ORF.

Construction of FLAG-Tagged FGF23.

pFGF23 and pR176Q were amplified separately with the primers forward (contains EcoRI site, underlined) 5'G GAATTCATATCCCAATGCCTCCCCA3' (SEQ ID NO:7) and reverse (contains BamHI site, underlined) 5'CG GGATCCCTAGATGAACTTGGCG3' (SEQ ID NO:6). The resulting cDNAs were digested with EcoRI and BamHI, and directionally ligated into the pFLAG-CMV-3 expression vector (Sigma-Aldrich, Inc., St. Louis, Mo.) to generate plasmids expressing FLAG-FGF23 and FLAG-R176Q. It should be noted that the parental pFLAG-CMV-3 vector uses the pre-protrypsin leader sequence to allow secretion of N-terminal FLAG tagged fusion proteins. The clone inserts were sequenced to confirm the proper reading frame of the fusion protein.

Heparin-Binding Assay.

Conditioned media (0.5 ml) obtained from transfected HEK293 cells was incubated 1:1 with 1×PBS, pH 7.4, as well as 50 μl of a 1:1 heparin sepharose: 1×PBS (Amersham Pharmacia, Inc., Piscataway, N.J.) suspension. The mixture was placed on a rotating platform at 4° C. for four hours, then centrifuged for 1 minute. The supernatant was removed, and the sepharose washed four times with ice cold 1×PBS. Laemmli sample buffer (50 μl) was added to the sepharose and the suspension was vortexed briefly, then boiled for 5 minutes. The sample was centrifuged for 1 minute and the supernatant was removed. Ten μl of the supernatant (material which bound heparin sepharose) was analyzed by Western blot analysis using an anti-FGF23 antibody.

The results of the experiments presented in this example are now described.

Figure 10A:
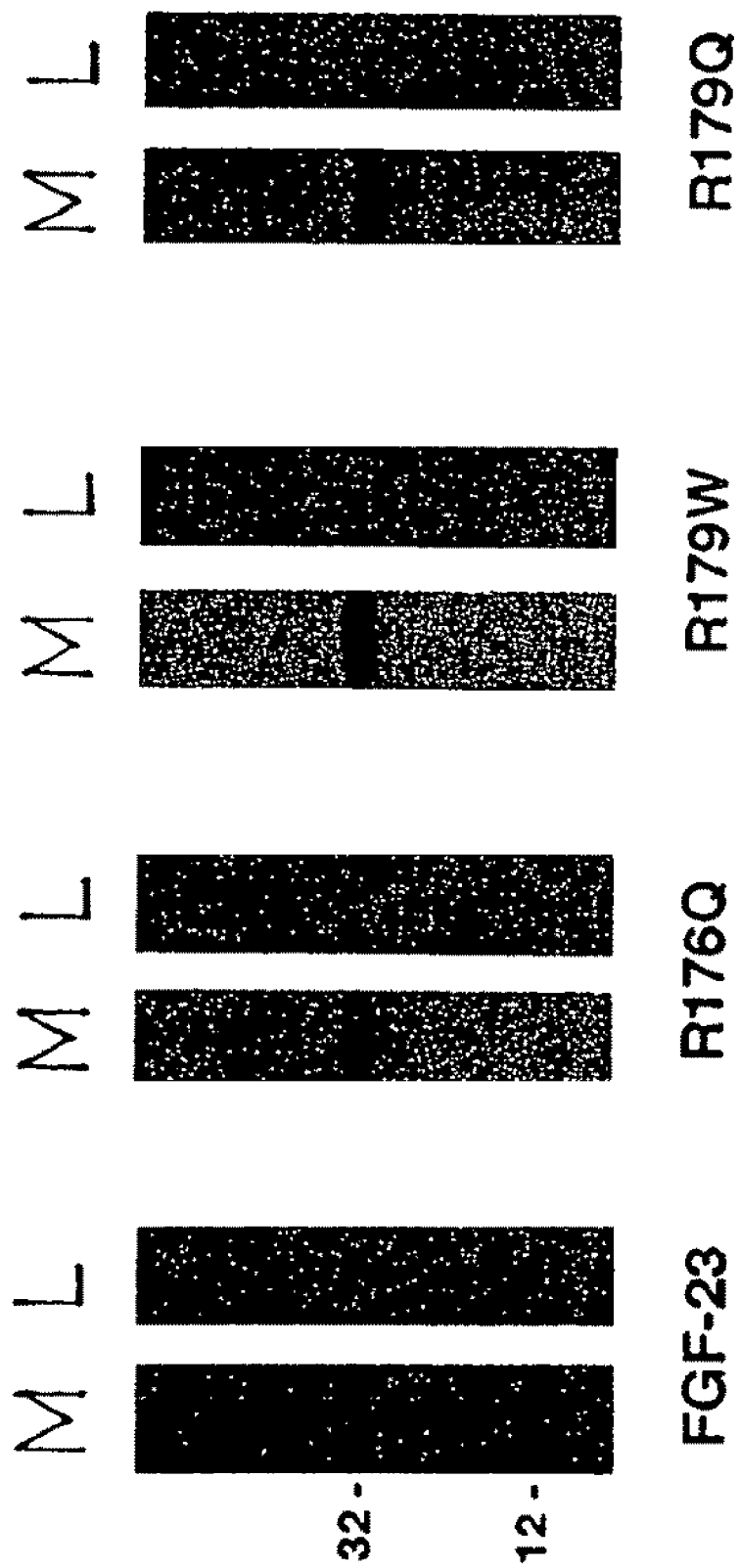
FIG. 10A is a series of images of Western blots depicting expression and secretion of wild-type and ADHR mutant forms of FGF23 protein. Western blot analysis using anti-FGF23 antibody and two micrograms of conditioned media (M) or fifty micrograms of cellular lysate (L) obtained from HEK293 cells transfected with plasmids expressing wild-type (FGF23) or ADHR mutant (R176Q, R179W, R179Q) forms of FGF23. Bands of 32 and 12 kDa were detected in conditioned media in the case of wild-type FGF23, whereas only the 32 kDa species was detected in the case of the ADHR mutants. Cellular lysates were negative for all FGF23 transfections, and all constructs exhibited similar transfection efficiencies.

To evaluate expression and secretion of ADHR mutant forms of FGF23 in mammalian cells, FGF23 expression plasmids containing the ADHR missense mutations (R176Q, R179W, R179Q) were constructed as described above. The predicted signal sequence and predicted protease cleavage site are indicated within the FGF23 amino acid sequence (FIG. 9). Expression and secretion of mutant FGF23 was analyzed by transfecting HEK293 cells with plasmids expressing wild-type FGF23, R176Q, R179Q, and R179W. Western blot analysis was performed on conditioned media and on total cellular lysates derived from transfected cells using a polyclonal antibody to human FGF23. Immunoreactive proteins of approximately 32 kDa and a doublet at 12 kDa were detected in the conditioned media obtained from the pFGF23-transfected cells (FIG. 10A). In contrast, only the 32 kDa band was detected in the conditioned media obtained from mutant pFGF23-transfected cells, and there was no apparent difference in the level of expression between wild-type and mutant FGF23 (FIG. 10A). In addition, total cellular lysates were negative for wild-type or mutant FGF23 protein, as were vector-control transfections (FIG. 10A). The amino acid changes in the mutant FGF23 proteins are shown in FIG. 10B. These results indicate that transiently transfected mammalian cell lines secrete FGF23 containing the human ADHR mutations. However, only the larger proteins species could be detected in media from cells expression the mutant forms of FGF23 using a polyclonal antibody. It should be noted that the epitope for the anti-FGF23 antibody is C-terminal to the potential SPC cleavage site at residues 176-179 present in the wild-type FGF23 protein, and thus, the 12 kDa bands may represent C-terminal fragments of the FGF23 32 kDa species. If the 12 kDa species is a break down product of the 32 kDa band, an antibody upstream of the SPC cleavage site should bind both the larger protein species as well as the N-terminal protein fragment.

Figure 11A:
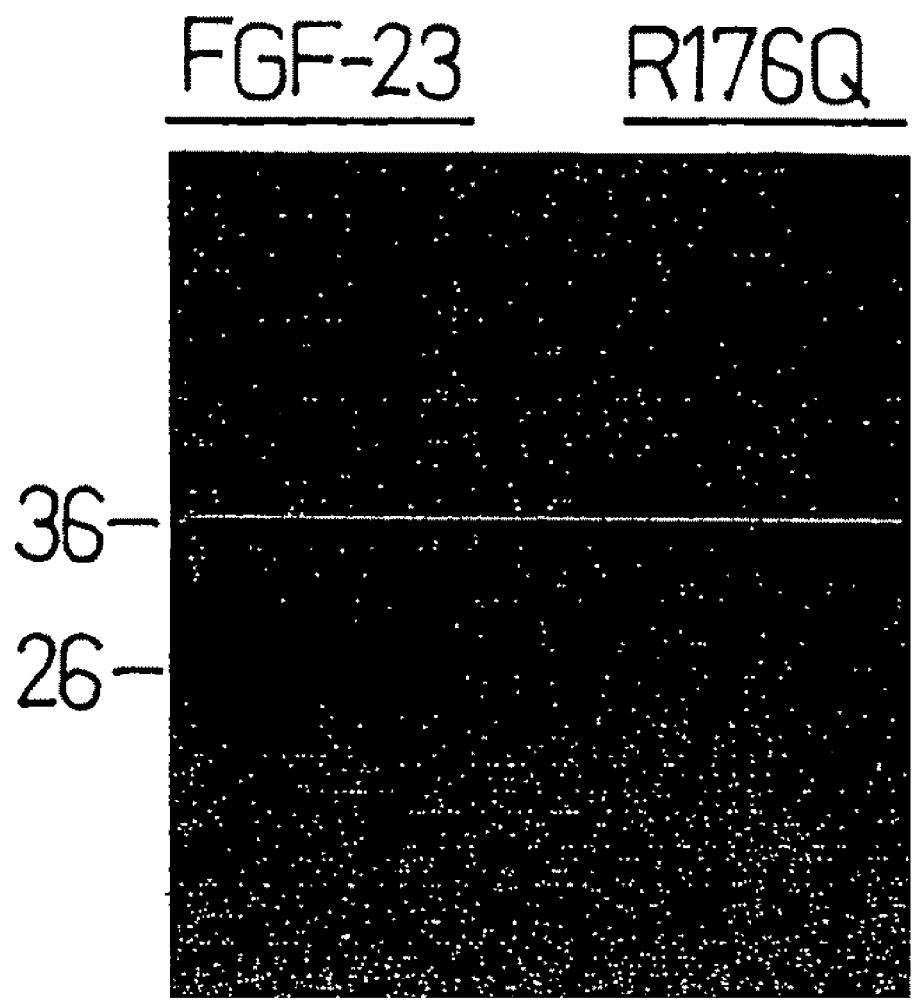
FIG. 11A is an image of a Western blot depicting expression of FLAG-tagged FGF23. Western blot analysis with a monoclonal antibody specific for FLAG (M2) was used to detect N-terminal FLAG-tagged wild-type (two individual clones, left two lanes) or R176Q mutant (two individual clones, right two lanes) FGF23 in conditioned media obtained from HEK293 cells transfected with plasmids expressing wild-type or R176Q mutant forms of FGF23. Wild-type FLAG-FGF23 was detected as a 36 kDa band and a pronounced 26 kDa fragment, whereas the FLAG-R176Q mutant resolved primarily as the 36 kDa species, with a faint band resolving at 26 kDa.
Figure 11B:
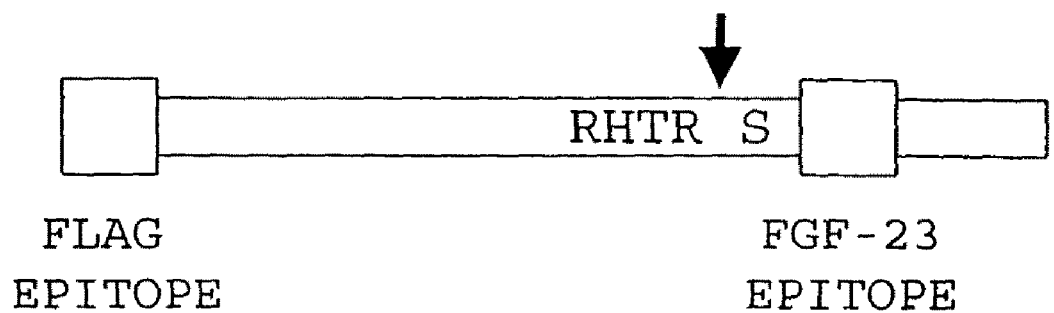
FIG. 11B is a diagram depicting the FGF23 protein where the relative positions of the FLAG epitope, the anti-FGF23 epitope, and the SPC site are shown.

This possibility was tested definitively using plasmids expressing N-terminal FLAG epitope-tagged wild-type and mutant (R176Q) FGF23 constructed as described above. To determine whether the FGF23 protein species were detectable with an antibody to the N-terminus of the protein, HEK293 cells were transiently transfected with a vector control, or plasmids expressing FLAG-FGF23 and FLAG-R176Q. The conditioned media obtained from transfected cells was analyzed by Western blotting using an anti-FLAG monoclonal antibody (M5; Sigma-Aldrich, Inc., St. Louis, Mo.). In conditioned media obtained from FLAG-FGF23-transfected cells, anti-FLAG antibody recognized two bands of 36 and 26 kDa, whereas in media from FLAG-R176Q-transfected cells, the antibody recognized primarily the 36 kDa band, with a very minor band detectable at 26 kDa (FIG. 11A). The vector control media produced no reactive bands nor did any of the cellular lysates. The larger FLAG-FGF23 protein species detected in the media migrated at 36 kDa, as opposed to 32 kDa as observed above, because of the additional residues from the FLAG tag. This was confirmed by Western blot analysis of the same media using the polyclonal anti-FGF23 antibody which detected the 36 kDa wild-type and mutant FLAG-tagged FGF23. The location of the FLAG epitope, anti-FGF23 epitope, and SPC cleavage site are shown in FIG. 11B. These results indicate that the smaller bands in Western blots from wild-type FGF23 are indeed C- and N-terminal fragments of FGF23, and that the ADHR mutant forms of FGF23 are secreted primarily as the larger protein species. These results indicate that the ADHR mutations at amino acids 176 and 179 stabilize the 32 kDa FGF23 protein species. Based on the observation that mutant forms of FGF23 that are associated with phosphate wasting in ADHR patients are not cleaved as efficiently as wild-type FGF23, stabilization and secretion of the full-length FGF23, as opposed to secretion of the proteolytic fragments, likely leads to renal phosphate wasting. In addition, these results suggest that ADHR mutations likely enhance, rather than inactivate, the biological activity of FGF23 in a phosphate wasting role.

Figure 12A:
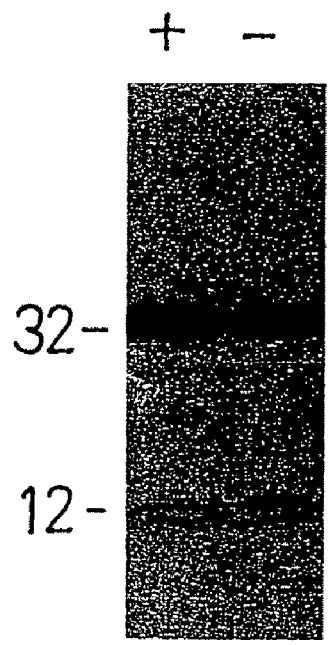
FIG. 12A is an image of a Western blot depicting extracellular exposure of FGF23 protein to HEK293 cells. Western blot analysis using an antibody specific for FGF23 was performed on FGF23 conditioned media that was incubated for 24 hours with $5 \times 10^6$ HEK293 cells (+) or in an empty culture dish (−). There was no difference in intensity of the 32 and 12 kDa bands after treatment.
Figure 12B:
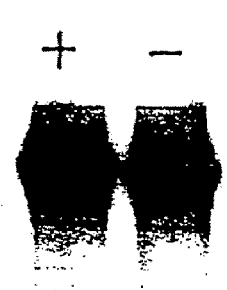
FIG. 12B is an image of a Coomassie blue-stained gel. The samples shown in FIG. 12A were electrophoresed in parallel, and Commassie staining confirmed equal gel loading.

To determine whether the cleavage of FGF23 observed using HEK293 cells occurred intra- or extracellularly, FGF23 conditioned media was incubated in the absence of cells or with control HEK293 cells (not expressing FGF23) for 24 hours at 37° C. in 5% $CO_2$. After incubation, media was collected, concentrated to equal volumes, and subjected to Western blot analysis using the C-terminal anti-FGF23 antibody. There was no change in the ratio of 32 kDa band to 12 kDa band regardless of treatment (FIG. 12A), indicating that cleavage of FGF23 occurred intracellularly, either before or during cellular secretion, and not by extracellular proteases expressed on HEK293 cells. Coomassie blue staining of the samples electrophoresed in parallel confirmed equal gel loading (FIG. 12B).

Figure 13:
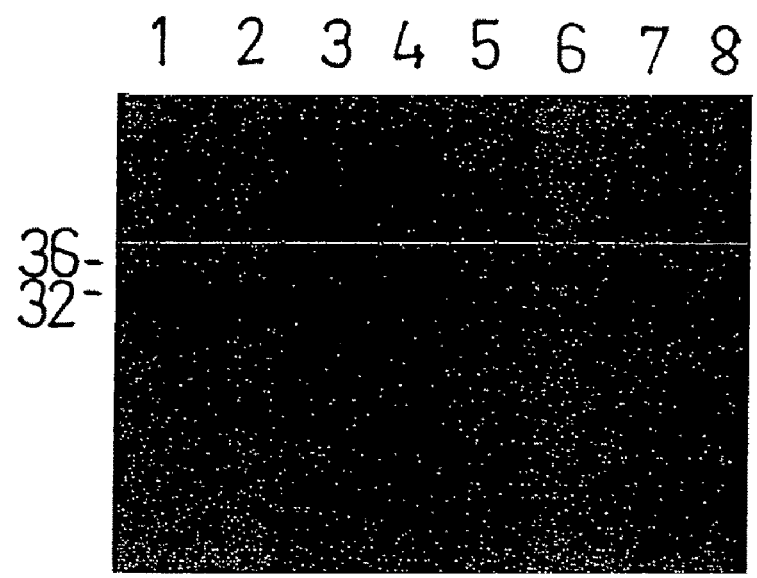
FIG. 13 is an image of a Western blot depicting binding of wild-type and ADHR mutant FGF23 to heparin. Conditioned media obtained from HEK293 cells transfected with wild-type or mutant forms of FGF23 and FLAG-tagged wild-type or mutant forms of FGF23 were incubated with heparin-sepharose, and the bound material was subjected to Western blot analysis with an anti-FGF23 antibody. The 32 kDa species corresponding to wild-type or mutant FGF23 bound heparin. In the case of the control vectors, the media was negative. The origin of the faint band at approximately 28 kDa in some samples is unknown. (Lane 1=native FGF23; lane 2=R176Q; lane 3=R179W; lane 4=R179Q; lane 5=CMV vector; lane 6=FLAG-FGF23; lane 7=FLAG-176Q; lane 8=FLAG vector.)

The ADHR mutations at R176 and R179 are adjacent to B strands that contain FGF heparin binding motifs. To test whether the ADHR mutations interfere with the ability of FGF23 to bind to heparin, conditioned media obtained from HEK293 cells transfected with plasmids expressing wild-type or mutant forms of FGF23 was incubated with heparin sepharose as described above. The 32 kDa protein species was detected in samples of wild type and mutant FGF23-transfected cell media, whereas samples of empty vector-transfected cell media was negative, indicating that both wild-type and mutant forms of FGF23 efficiently bound heparin (FIG. 13). In similar experiments using media obtained from cells transfected with plasmids expressing FLAG-tagged FGF23, the 36 kDa species of FLAG-tagged wild-type and mutant FGF23 also bound heparin (FIG. 13). These results demonstrate that the FGF23 32 kDa species specifically binds heparin, and provide biochemical evidence that FGF23 is indeed a member of the heparin-binding FGF family. In addition, the observation that mutant forms of FGF23 retain heparin binding indicates that the ADHR missense mutations do not grossly alter the protein structure of FGF23.

Example 4

FGF23 Analysis in Mice

The data herein demonstrate the generation and analysis of mice which overexpress FGF23, express mutant forms of FGF23, or are exposed to phosphate-depleted or phosphate-enriched diets.

To assess the correlation between FGF23 expression and altered phosphate homeostasis in mice, transgenic mice that overexpress murine FGF23 in the liver are constructed and phosphorous concentrations in serum and urine samples from transgenic and control mice are compared. Mice are weighed and examined regularly to determine if there are any outward phenotypic differences. Consistent with overexpression of FGF23 in human tumors associated with renal phosphate wasting, transgenic mice which overexpress FGF23 should exhibit renal phosphate wasting and resulting hypophosphatemia. Moreover, these mice should display decreased levels of Npt2 (the main sodium dependent phosphate transporter) mRNA and protein in the kidney. Levels of serum 1, 25 dihydroxy vitamin D concentrations are compared between FGF23 transgenic mice, control mice, and control mice that have equivalent serum phosphate concentration that are induced by dietary phosphate depletion or excess. Similarly, mice injected with purified FGF23 should display renal phosphate wasting and become hypophosphatemic.

Transgenic mice comprising the same mutations observed in human ADHR patients (R176Q, R179Q, R179W, or any other mutation in arginines 176 or 179) are constructed and should serve as good animal models for the human disorder. As described above, serum and urine phosphorous as well as serum 1,25 dihydroxy vitamin D concentrations will be examined. Mice heterozygous for the mutation should manifest renal phosphate wasting and hypophosphatemia in common with humans who have ADHR, whereas mice that are homozygous for the mutation should have a more severe phenotype. Mutant mice should also display decreased levels of Npt2 mRNA and protein in the kidney.

Administration of a phosphate-depleted or phosphate-enriched diet to mice alters serum phosphate concentrations and should alter FGF23 expression levels in thyroid/parathyroid, heart, or liver. Hyperphosphatemia should increase expression of FGF23 mRNA in these tissues, whereas hypophosphatemia should decrease expression of FGF23 mRNA in these tissues.

Levels of FGF23 expression in male and female Hyp mice, which have mutations in the Phex gene and are the murine model of human X-linked hypophosphatemic rickets, is compared to that in normal littermate controls or littermates with phosphate-altered diet. Hyp mice should have increased expression and serum concentrations of FGF23.

Example 5

Detection of FGF23 in Tumor Induced Osteomalacia Patients

The data herein demonstrate the use of an FGF23 detection protocol to diagnose tumor induced osteomalacia in a patient.

A tumor is surgically excised from a patient exhibiting the clinical symptoms of tumor induced osteomalacia. The tumor cells are then grown in cell culture flasks for 48 hours. RNA is isolated from the tumor cells using standard protocols. RT-PCR is performed on RNA from the tumor using PCR primers specific for FGF23. A cDNA band of the appropriate size is amplified from RNA from the tumor, but not from tumor cell RNA that was not subject to reverse transcription prior to PCR (negative control). Thus, detection of FGF23 mRNA in the tumor sample is indicative of tumor induced osteomalacia, and thereby serves as a valuable diagnostic tool for this disease.

Example 6

Safety of FGF23 in Humans

The data herein demonstrate the safety of FGF23 in humans.

In some patients with tumor induced osteomalacia, tumors are not detectable. Upon treatment with high doses of 1,25 dihydroxy vitamin D and phosphate, the condition of these patients improves. Once the hypophosphatemia is corrected in these patients, no symptoms remain despite the fact that the concentration of FGF23 in their blood is very high. The same is true in ADHR patients, all of whom presumably have high FGF23 serum concentrations secondary to their inability to degrade the mutant FGF23. Thus, high levels of FGF23 have no apparent ill effects in humans.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A kit for diagnosing a hypophosphatemic disorder in a mammal, said kit comprising an antibody that detects a polypeptide comprising the amino acid sequence of SEQ ID NO:2, wherein an elevated level of said detected polypeptide is an indication that said mammal is afflicted with said hypophosphatemic disorder, wherein said hypophosphatemic disorder is selected from the group consisting of X-linked hypophosphatemic rickets and tumor induced osteomalacias.

* * * * *

SEQUENCE LISTING

<160> NUMBER OF SEQ ID NOS: 35

<210> SEQ ID NO 1
<211> LENGTH: 1612
<212> TYPE: DNA
<213> ORGANISM: Homo sapiens

<400> SEQUENCE: 1

```
cggcaaaaag gagggaatcc agtctaggat cctcacacca gctacttgca agggagaagg      60
aaaaggccag taaggcctgg gccaggagag tcccgacagg agtgtcaggt ttcaatctca     120
gcaccagcca ctcagagcag ggcacgatgt tgggggcccg cctcaggctc tgggtctgtg     180
ccttgtgcag cgtctgcagc atgagcgtcc tcagagccta tcccaatgcc tccccactgc     240
tcggctccag ctggggtggc ctgatccacc tgtacacagc cacagccagg aacagctacc     300
acctgcagat ccacaagaat ggccatgtgg atggcgcacc ccatcagacc atctacagtg     360
ccctgatgat cagatcagag gatgctggct ttgtggtgat acaggtgtg atgagcagaa      420 gatacctctg catggatttc agaggcaaca ttttggatc acactatttc gacccggaga      480
actgcaggtt ccaacaccag acgctggaaa acgggtacga cgtctaccac tctcctcagt     540
atcacttcct ggtcagtctg gccgggcga agagagcctt cctgccaggc atgaacccac     600
ccccgtactc ccagttcctg tcccggagga acgagatccc cctaattcac ttcaacaccc     660
ccataccacg gcggcacacc cggagcgccg aggacgactc ggagcgggac ccctgaacg      720 tgctgaagcc ccgggcccgg atgaccccgg ccccggcctc ctgttcacag gagctcccga     780
gcgccgagga caacagcccg atggccagtg acccattagg ggtggtcagg ggcggtcgag     840
tgaacacgca cgctggggga acgggcccgg aaggctgccg cccttcgcc aagttcatct      900 agggtcgctg gaagggcacc ctctttaacc catccctcag caaacgcagc tcttcccaag     960
gaccaggtcc cttgacgttc cgaggatggg aaaggtgaca gggcatgta tggaatttgc     1020 tgcttctctg gggtccttc cacaggaggt cctgtgagaa ccaacctttg aggcccaagt     1080 catgggttt caccgccttc ctcactccat atagaacacc tttcccaata ggaaacccca     1140
acaggtaaac tagaaatttc cccttcatga aggtagagag aagggtctc tcccaacata     1200 tttctcttcc ttgtgcctct cctctttatc acttttaagc ataaaaaaa aaaaaaaaa     1260 aaaaaaaaaa aaaagcagtg ggttcctgag ctcaagactt tgaaggtgta gggaagagga     1320
aatcggagat cccagaagct tctccactgc cctatgcatt tatgttagat gccccgatcc     1380
cactggcatt tgagtgtgca aaccttgaca ttaacagctg aatgggcaa gttgatgaaa      1440 acactacttt caagccttcg ttcttccttg agcatctctg gggaagagct gtcaaaagac     1500
tggtggtagg ctggtgaaaa cttgacagct agacttgatg cttgctgaaa tgaggcagga     1560
atcataatag aaaactcagc ctccctacag ggtgagcacc ttctgtctcg ct              1612
```

<210> SEQ ID NO 2
<211> LENGTH: 251
<212> TYPE: PRT
<213> ORGANISM: Homo sapiens

<400> SEQUENCE: 2

```
Met Leu Gly Ala Arg Leu Arg Leu Trp Val Cys Ala Leu Cys Ser Val
1               5                   10                  15

Cys Ser Met Ser Val Leu Arg Ala Tyr Pro Asn Ala Ser Pro Leu Leu
            20                  25                  30
```

-continued

```
Gly Ser Ser Trp Gly Gly Leu Ile His Leu Tyr Thr Ala Thr Ala Arg
            35                  40                  45
Asn Ser Tyr His Leu Gln Ile His Lys Asn Gly His Val Asp Gly Ala
 50                  55                  60
Pro His Gln Thr Ile Tyr Ser Ala Leu Met Ile Arg Ser Glu Asp Ala
 65                  70                  75                  80
Gly Phe Val Val Ile Thr Gly Val Met Ser Arg Arg Tyr Leu Cys Met
                     85                  90                  95
Asp Phe Arg Gly Asn Ile Phe Gly Ser His Tyr Phe Asp Pro Glu Asn
                100                 105                 110
Cys Arg Phe Gln His Gln Thr Leu Glu Asn Gly Tyr Asp Val Tyr His
            115                 120                 125
Ser Pro Gln Tyr His Phe Leu Val Ser Leu Gly Arg Ala Lys Arg Ala
130                 135                 140
Phe Leu Pro Gly Met Asn Pro Pro Tyr Ser Gln Phe Leu Ser Arg
145                 150                 155                 160
Arg Asn Glu Ile Pro Leu Ile His Phe Asn Thr Pro Ile Pro Arg Arg
                165                 170                 175
His Thr Arg Ser Ala Glu Asp Ser Glu Arg Asp Pro Leu Asn Val
            180                 185                 190
Leu Lys Pro Arg Ala Arg Met Thr Pro Ala Pro Ala Ser Cys Ser Gln
            195                 200                 205
Glu Leu Pro Ser Ala Glu Asp Asn Ser Pro Met Ala Ser Asp Pro Leu
210                 215                 220
Gly Val Val Arg Gly Gly Arg Val Asn Thr His Ala Gly Gly Thr Gly
225                 230                 235                 240
Pro Glu Gly Cys Arg Pro Phe Ala Lys Phe Ile
                245                 250

<210> SEQ ID NO 3
<211> LENGTH: 1559
<212> TYPE: DNA
<213> ORGANISM: Mus sp.

<400> SEQUENCE: 3
agcctgtctg ggagtgtcag atttcaaact cagcattagc cactcagtgc tgtgcaatgc      60
tagggacctg ccttagactc ctggtgggcg tgctctgcac tgtctgcagc ttgggcactg     120
ctagagccta tccggacact tccccattgc ttggctccaa ctggggaagc ctgacccacc     180
tgtacacggc tacagccagg accagctatc acctacagat ccatagggat ggtcatgtag     240
atggcacccc ccatcagacc atctacagtg ccctgatgat tacatcagag gacgccggct     300
ctgtggtgat aacaggagcc atgactcgaa ggttcctttg tatggatctc cacggcaaca     360
tttttggatc gcttcacttc agcccagaga attgcaagtt ccgccagtgg acgctggaga     420
atggctatga cgtctacttg tcgcagaagc atcactacct ggtgagcctg gccgcgccaa     480
agcgcatctt ccagccgggc accaacccgc cgccttctc ccagttcctg gctcgcagga     540
acgaggtccc gctgctgcat ttctacactg ttcgcccacg cgccacacg cgcagcgccg     600
aggacccacc ggagcgcgac ccactgaacg tgctcaagcc gcggccccgc gccacgcctg     660
tgcctgtatc ctgctctcgc gagctgccga gcgcagagga aggtggcccc gcagccagcg     720
atcctctggg ggtgctgcgc agaggccgtg gagatgctcg cggggcgcg ggaggcgcgg     780
ataggtgtcg cccctttccc aggttcgtct aggtccccag gccaggctgc gtccgcctcc     840
atcctccagt cggttcagcc cacgtagagg aaggactagg gtacctcgag gatgtctgct     900
```

-continued

```
tctctcccctt ccctatgggc ctgagagtca cctgcgaggt tccagccagg caccgctatt    960
cagaattaag agccaacggt gggaggctgg agaggtggcg cagacagttc tcagcaccca   1020
caaatacctg taattctagc tccaggggaa tctgtactca cacacacaca catccacaca   1080
cacacacaca cacatacatg taattttaaa tgttaatctg atttaaagac cccaacaggt   1140
aaactagaca cgaagctctt tttatttat tttactaaca ggtaaaccag acacttggcc    1200
tttattagcc gggtctcttg cctagcattt taatcgatca gttagcacga ggaaagagtt   1260
cacgccttga acacagggaa gaggccatct ctgcagcttc tagttactat tctgggattc   1320
acgggtgttt gagtttgagc accttgacct taatgtcttc actaggcaag tcgaagaaag   1380
acgcgcattt cttctctttg ggaagagctt tggattggcg ggaggctgac aaggacacct   1440
aaaccgaaca catttcagag ttcagcctcc ctgaggaatg attcgccaat gattctgtga   1500
taggaccagt cagtagcttt tgaatttgcc ctggctcagc aaagtctacc ttgctaggg    1559
```

<210> SEQ ID NO 4
<211> LENGTH: 251
<212> TYPE: PRT
<213> ORGANISM: Mus sp.

<400> SEQUENCE: 4

```
Met Leu Gly Thr Cys Leu Arg Leu Leu Val Gly Val Leu Cys Thr Val
1               5                   10                  15

Cys Ser Leu Gly Thr Ala Arg Ala Tyr Pro Asp Thr Ser Pro Leu Leu
            20                  25                  30

Gly Ser Asn Trp Gly Ser Leu Thr His Leu Tyr Thr Ala Thr Ala Arg
        35                  40                  45

Thr Ser Tyr His Leu Gln Ile His Arg Asp Gly His Val Asp Gly Thr
    50                  55                  60

Pro His Gln Thr Ile Tyr Ser Ala Leu Met Ile Thr Ser Glu Asp Ala
65                  70                  75                  80

Gly Ser Val Val Ile Thr Gly Ala Met Thr Arg Arg Phe Leu Cys Met
                85                  90                  95

Asp Leu His Gly Asn Ile Phe Gly Ser Leu His Phe Ser Pro Glu Asn
            100                 105                 110

Cys Lys Phe Arg Gln Trp Thr Leu Glu Asn Gly Tyr Asp Val Tyr Leu
        115                 120                 125

Ser Gln Lys His His Tyr Leu Val Ser Leu Gly Arg Ala Lys Arg Ile
    130                 135                 140

Phe Gln Pro Gly Thr Asn Pro Pro Phe Ser Gln Phe Leu Ala Arg
145                 150                 155                 160

Arg Asn Glu Val Pro Leu Leu His Phe Tyr Thr Val Arg Pro Arg Arg
                165                 170                 175

His Thr Arg Ser Ala Glu Asp Pro Pro Glu Arg Asp Pro Leu Asn Val
            180                 185                 190

Leu Lys Pro Arg Pro Arg Ala Thr Pro Val Pro Val Ser Cys Ser Arg
        195                 200                 205

Glu Leu Pro Ser Ala Glu Glu Gly Gly Pro Ala Ala Ser Asp Pro Leu
    210                 215                 220

Gly Val Leu Arg Arg Gly Arg Gly Asp Ala Arg Gly Gly Ala Gly Gly
225                 230                 235                 240

Ala Asp Arg Cys Arg Pro Phe Pro Arg Phe Val
                245                 250
```

```
<210> SEQ ID NO 5
<211> LENGTH: 17
<212> TYPE: PRT
<213> ORGANISM: Homo sapiens

<400> SEQUENCE: 5

Cys Ser Gln Glu Leu Pro Ser Ala Glu Asp Asn Ser Pro Met Ala Ser
1               5                   10                  15

Asp

<210> SEQ ID NO 6
<211> LENGTH: 25
<212> TYPE: DNA
<213> ORGANISM: Homo sapiens

<400> SEQUENCE: 6
cgggatccac gatgttgggg gcccg                                       25

<210> SEQ ID NO 7
<211> LENGTH: 25
<212> TYPE: DNA
<213> ORGANISM: Homo sapiens

<400> SEQUENCE: 7
ggaattccta gatgaacttg gcgaa                                       25

<210> SEQ ID NO 8
<211> LENGTH: 21
<212> TYPE: DNA
<213> ORGANISM: Homo sapiens

<400> SEQUENCE: 8
ataccacggc agcacacccg g                                           21

<210> SEQ ID NO 9
<211> LENGTH: 21
<212> TYPE: DNA
<213> ORGANISM: Homo sapiens

<400> SEQUENCE: 9
ccgggtgtgc tgccgtggta t                                           21

<210> SEQ ID NO 10
<211> LENGTH: 21
<212> TYPE: DNA
<213> ORGANISM: Homo sapiens

<400> SEQUENCE: 10
gcggcacacc tggagcgccg a                                           21

<210> SEQ ID NO 11
<211> LENGTH: 21
<212> TYPE: DNA
<213> ORGANISM: Homo sapiens

<400> SEQUENCE: 11
tcggcgctcc aggtgtgccg c                                           21

<210> SEQ ID NO 12
<211> LENGTH: 21
<212> TYPE: DNA
<213> ORGANISM: Homo sapiens
```

-continued

```
<400> SEQUENCE: 12
cggcacaccc agagcgccga g                                              21

<210> SEQ ID NO 13
<211> LENGTH: 21
<212> TYPE: DNA
<213> ORGANISM: Homo sapiens

<400> SEQUENCE: 13
ctcggcgctc tgggtgtgcc g                                              21

<210> SEQ ID NO 14
<211> LENGTH: 139
<212> TYPE: PRT
<213> ORGANISM: Homo Sapiens

<400> SEQUENCE: 14
```

Leu Lys Gly Ile Val Thr Arg Leu Phe Ser Gln Gln Gly Tyr Phe Leu
1               5                   10                  15

Gln Met His Pro Asp Gly Thr Ile Asp Gly Thr Lys Asp Glu Asn Ser
            20                  25                  30

Asp Tyr Thr Leu Phe Asn Leu Ile Pro Val Gly Leu Arg Val Val Ala
        35                  40                  45

Ile Gln Gly Val Lys Ala Ser Leu Tyr Val Ala Met Asn Gly Glu Gly
    50                  55                  60

Tyr Leu Tyr Ser Ser Asp Val Phe Thr Pro Glu Cys Lys Phe Lys Glu
65                  70                  75                  80

Ser Val Phe Glu Asn Tyr Tyr Val Ile Tyr Ser Ser Thr Leu Tyr Arg
                85                  90                  95

Gln Gln Glu Ser Gly Arg Ala Trp Phe Leu Gly Leu Asn Lys Glu Gly
            100                 105                 110

Gln Ile Met Lys Gly Asn Arg Val Lys Lys Thr Lys Pro Ser Ser His
        115                 120                 125

Phe Val Pro Lys Pro Ile Glu Val Cys Met Tyr
    130                 135

```
<210> SEQ ID NO 15
<211> LENGTH: 139
<212> TYPE: PRT
<213> ORGANISM: Homo Sapiens

<400> SEQUENCE: 15
```

Leu Lys Gly Ile Val Thr Arg Leu Tyr Cys Arg Gln Gly Tyr Tyr Leu
1               5                   10                  15

Gln Met His Pro Asp Gly Ala Leu Asp Gly Thr Lys Asp Asp Ser Thr
            20                  25                  30

Asn Ser Thr Leu Phe Asn Leu Ile Pro Val Gly Leu Arg Val Val Ala
        35                  40                  45

Ile Gln Gly Val Lys Thr Gly Leu Tyr Ile Ala Met Asn Gly Glu Gly
    50                  55                  60

Tyr Leu Tyr Pro Ser Glu Leu Phe Thr Pro Glu Cys Lys Phe Lys Glu
65                  70                  75                  80

Ser Val Phe Glu Asn Tyr Tyr Val Ile Tyr Ser Ser Met Leu Tyr Arg
                85                  90                  95

Gln Gln Glu Ser Gly Arg Ala Trp Phe Leu Gly Leu Asn Lys Glu Gly
            100                 105                 110

```
Gln Ala Met Lys Gly Asn Arg Val Lys Lys Thr Lys Pro Ala Ala His
            115                 120                 125
Phe Leu Pro Lys Pro Leu Glu Val Ala Met Tyr
        130                 135

<210> SEQ ID NO 16
<211> LENGTH: 139
<212> TYPE: PRT
<213> ORGANISM: Homo Sapiens

<400> SEQUENCE: 16

Leu Lys Gly Ile Val Thr Lys Leu Tyr Ser Arg Gln Gly Tyr His Leu
1               5                   10                  15
Gln Leu Gln Ala Asp Gly Thr Ile Asp Gly Thr Lys Asp Glu Asp Ser
            20                  25                  30
Thr Tyr Thr Leu Phe Asn Leu Ile Pro Val Gly Leu Arg Val Val Ala
        35                  40                  45
Ile Gln Gly Val Gln Thr Lys Leu Tyr Leu Ala Met Asn Ser Glu Gly
    50                  55                  60
Tyr Leu Tyr Thr Ser Glu Leu Phe Thr Pro Glu Cys Lys Phe Lys Glu
65                  70                  75                  80
Ser Val Phe Glu Asn Tyr Tyr Val Thr Tyr Ser Ser Met Ile Tyr Arg
                85                  90                  95
Gln Gln Gln Ser Gly Arg Gly Trp Tyr Leu Gly Leu Asn Lys Glu Gly
            100                 105                 110
Glu Ile Met Lys Gly Asn His Val Lys Lys Asn Lys Pro Ala Ala His
            115                 120                 125
Phe Leu Pro Lys Pro Leu Lys Val Ala Met Tyr
        130                 135

<210> SEQ ID NO 17
<211> LENGTH: 139
<212> TYPE: PRT
<213> ORGANISM: Homo Sapiens

<400> SEQUENCE: 17

Leu Lys Gly Ile Val Thr Lys Leu Phe Cys Arg Gln Gly Phe Tyr Leu
1               5                   10                  15
Gln Ala Asn Pro Asp Gly Ser Ile Gln Gly Thr Pro Glu Asp Thr Ser
            20                  25                  30
Ser Phe Thr His Phe Asn Leu Ile Pro Val Gly Leu Arg Val Val Thr
        35                  40                  45
Ile Gln Ser Ala Lys Leu Gly His Tyr Met Ala Met Asn Ala Glu Gly
    50                  55                  60
Leu Leu Tyr Ser Ser Pro His Phe Thr Ala Glu Cys Arg Phe Lys Glu
65                  70                  75                  80
Cys Val Phe Glu Asn Tyr Tyr Val Leu Tyr Ala Ser Ala Leu Tyr Arg
                85                  90                  95
Gln Arg Arg Ser Gly Arg Ala Trp Tyr Leu Gly Leu Asp Lys Glu Gly
            100                 105                 110
Gln Val Met Lys Gly Asn Arg Val Lys Lys Thr Lys Ala Ala Ala His
            115                 120                 125
Phe Leu Pro Lys Leu Leu Glu Val Ala Met Tyr
        130                 135
```

```
<210> SEQ ID NO 18
<211> LENGTH: 141
<212> TYPE: PRT
<213> ORGANISM: Homo Sapiens

<400> SEQUENCE: 18

Leu Lys Gly Ile Leu Arg Arg Gln Leu Tyr Cys Arg Thr Gly Phe
1               5                   10                  15

His Leu Glu Ile Phe Pro Asn Gly Thr Val His Gly Thr Arg His Asp
            20                  25                  30

His Ser Arg Phe Gly Ile Leu Glu Phe Ile Ser Leu Ala Val Gly Leu
        35                  40                  45

Ile Ser Ile Arg Gly Val Asp Ser Gly Leu Tyr Leu Gly Met Asn Glu
    50                  55                  60

Arg Gly Glu Leu Tyr Gly Ser Lys Lys Leu Thr Arg Glu Cys Val Phe
65                  70                  75                  80

Arg Glu Gln Phe Glu Glu Asn Tyr Asn Asn Thr Tyr Ala Ser Thr Leu
                85                  90                  95

Tyr Lys His Ser Asp Ser Glu Arg Gln Tyr Tyr Val Ala Leu Asn Lys
                100                 105                 110

Asp Gly Ser Pro Arg Glu Gly Tyr Arg Thr Lys Arg His Gln Lys Phe
            115                 120                 125

Thr His Phe Leu Pro Arg Pro Val Asp Pro Ser Lys Leu
        130                 135                 140

<210> SEQ ID NO 19
<211> LENGTH: 141
<212> TYPE: PRT
<213> ORGANISM: Homo Sapiens

<400> SEQUENCE: 19

Leu Lys Gly Ile Leu Arg Arg Gln Leu Tyr Cys Arg Thr Gly Phe
1               5                   10                  15

His Leu Glu Ile Phe Pro Asn Gly Thr Ile Gln Gly Thr Arg Lys Asp
            20                  25                  30

His Ser Arg Phe Gly Ile Leu Glu Phe Ile Ser Ile Ala Val Gly Leu
        35                  40                  45

Val Ser Ile Arg Gly Val Asp Ser Gly Leu Tyr Leu Gly Met Asn Glu
    50                  55                  60

Lys Gly Glu Leu Tyr Gly Ser Glu Lys Leu Thr Gln Glu Cys Val Phe
65                  70                  75                  80

Arg Glu Gln Phe Glu Glu Asn Trp Tyr Asn Thr Tyr Ser Ser Asn Leu
                85                  90                  95

Tyr Lys His Val Thr Thr Gly Arg Arg Tyr Tyr Val Ala Leu Asn Lys
                100                 105                 110

Asp Gly Thr Pro Arg Glu Gly Thr Arg Thr Lys Arg His Gln Lys Phe
            115                 120                 125

Thr His Phe Leu Pro Arg Pro Val Asp Pro Asp Lys Val
        130                 135                 140

<210> SEQ ID NO 20
<211> LENGTH: 135
<212> TYPE: PRT
<213> ORGANISM: Homo Sapiens
```

-continued

```
<400> SEQUENCE: 20

Leu Gln Gly Asp Val Arg Trp Arg Lys Leu Phe Ser Phe Thr Lys Tyr
1               5                   10                  15

Phe Leu Lys Ile Glu Lys Asn Gly Lys Val Ser Gly Thr Lys Lys Glu
            20                  25                  30

Asn Cys Pro Tyr Ser Ile Leu Glu Ile Thr Ser Val Glu Ile Gly Val
        35                  40                  45

Val Ala Val Lys Ala Ile Asn Ser Asn Tyr Tyr Leu Ala Met Asn Lys
    50                  55                  60

Lys Gly Lys Leu Tyr Gly Ser Lys Glu Phe Asn Asn Asp Cys Lys Leu
65                  70                  75                  80

Lys Glu Arg Ile Glu Glu Asn Gly Tyr Asn Thr Tyr Ala Ser Phe Asn
                85                  90                  95

Trp Gln His Asn Gly Gln Met Tyr Val Ala Leu Asn Gly Tyr Gly Ala
            100                 105                 110

Pro Arg Arg Gly Gln Lys Thr Arg Arg Lys Asn Thr Ser Ala His Phe
        115                 120                 125

Leu Pro Met Val Val His Ser
    130                 135

<210> SEQ ID NO 21
<211> LENGTH: 136
<212> TYPE: PRT
<213> ORGANISM: Homo Sapiens

<400> SEQUENCE: 21

Met Glu Gly Gly Asp Ile Arg Val Arg Arg Leu Phe Cys Arg Thr Gln
1               5                   10                  15

Trp Tyr Leu Arg Ile Asp Lys Arg Gly Lys Val Lys Gly Thr Gln Glu
            20                  25                  30

Met Lys Asn Asn Tyr Asn Ile Met Glu Ile Arg Thr Val Ala Val Gly
        35                  40                  45

Ile Val Ala Ile Lys Gly Val Glu Ser Glu Phe Tyr Leu Ala Met Asn
    50                  55                  60

Lys Glu Gly Lys Leu Tyr Ala Lys Glu Lys Cys Asn Glu Asp Cys Asn
65                  70                  75                  80

Phe Lys Glu Leu Ile Leu Glu Asn His Tyr Asn Thr Tyr Ala Ser Ala
                85                  90                  95

Lys Trp Thr His Asn Gly Gly Glu Met Phe Val Ala Leu Asn Gln Lys
            100                 105                 110

Gly Ile Pro Val Arg Gly Lys Lys Thr Lys Lys Glu Gln Lys Thr Ala
        115                 120                 125

His Phe Leu Pro Met Ala Ile Thr
    130                 135

<210> SEQ ID NO 22
<211> LENGTH: 150
<212> TYPE: PRT
<213> ORGANISM: Homo Sapiens

<400> SEQUENCE: 22

Leu Gly Gly Ala Pro Arg Arg Arg Lys Leu Tyr Cys Ala Thr Lys Tyr
1               5                   10                  15

His Leu Gln Leu His Pro Ser Gly Arg Val Asn Gly Ser Leu Glu Asn
            20                  25                  30

Ser Ala Tyr Ser Ile Leu Glu Ile Thr Ala Val Glu Val Gly Ile Val
        35                  40                  45
```

```
Ala Ile Arg Gly Leu Phe Ser Gly Arg Tyr Leu Ala Met Asn Lys Arg
    50                  55                  60

Gly Arg Leu Tyr Ala Ser Glu His Tyr Ser Ala Glu Cys Glu Phe Val
65                  70                  75                  80

Glu Arg Ile His Glu Leu Gly Tyr Asn Thr Tyr Ala Ser Arg Leu Tyr
                85                  90                  95

Arg Thr Val Ser Ser Thr Pro Gly Ala Arg Arg Gln Pro Ser Ala Glu
            100                 105                 110

Arg Leu Trp Tyr Val Ser Val Asn Gly Lys Gly Arg Pro Arg Arg Gly
        115                 120                 125

Phe Lys Thr Arg Arg Thr Gln Lys Ser Ser Leu Phe Leu Pro Arg Val
    130                 135                 140

Leu Asp His Arg Asp His
145                 150

<210> SEQ ID NO 23
<211> LENGTH: 137
<212> TYPE: PRT
<213> ORGANISM: Homo Sapiens

<400> SEQUENCE: 23

Pro Pro Gly Asn Tyr Lys Lys Pro Lys Leu Leu Tyr Cys Ser Asn Gly
1               5                   10                  15

Gly Ser Phe Leu Arg Ile Leu Pro Asp Gly Thr Val Asp Gly Thr Arg
            20                  25                  30

Asp Arg Ser Asp Gln His Ile Gln Leu Gln Leu Ser Ala Glu Ser Val
        35                  40                  45

Gly Glu Val Tyr Ile Lys Ser Thr Glu Thr Gly Gln Tyr Leu Ala Met
    50                  55                  60

Asp Thr Asp Gly Leu Leu Tyr Gly Ser Gln Thr Pro Asn Glu Glu Cys
65                  70                  75                  80

Leu Phe Leu Glu Arg Leu Glu Glu Glu His Tyr Asn Thr Tyr Ile Ser
                85                  90                  95

Lys Lys His Ala Glu Lys Asn Trp Phe Val Gly Leu Lys Lys Asn Gly
            100                 105                 110

Ser Cys Lys Arg Gly Pro Arg Thr His Tyr Gly Gln Lys Ala Ile Leu
        115                 120                 125

Phe Leu Pro Leu Pro Val Ser Ser Asp
    130                 135

<210> SEQ ID NO 24
<211> LENGTH: 134
<212> TYPE: PRT
<213> ORGANISM: Homo Sapiens

<400> SEQUENCE: 24

Pro Pro Gly His Phe Lys Asp Pro Lys Arg Leu Tyr Cys Lys Asn Gly
1               5                   10                  15

Gly Phe Phe Leu Arg Ile His Pro Asp Gly Arg Val Asp Gly Val Arg
            20                  25                  30

Glu Lys Ser Asp Pro His Ile Lys Leu Gln Leu Gln Ala Glu Glu Arg
        35                  40                  45

Gly Val Val Ser Ile Lys Gly Val Cys Ala Asn Arg Tyr Leu Ala Met
    50                  55                  60

Lys Glu Asp Gly Arg Leu Leu Ala Ser Lys Cys Val Thr Asp Glu Cys
65                  70                  75                  80
```

```
Phe Phe Phe Glu Arg Leu Glu Ser Asn Asn Tyr Asn Thr Tyr Arg Ser
                85                  90                  95

Arg Lys Tyr Thr Ser Trp Tyr Val Ala Leu Lys Arg Thr Gly Gln Tyr
            100                 105                 110

Lys Leu Gly Ser Lys Thr Gly Pro Gly Gln Lys Ala Ile Leu Phe Leu
        115                 120                 125

Pro Met Ser Ala Lys Ser
        130

<210> SEQ ID NO 25
<211> LENGTH: 130
<212> TYPE: PRT
<213> ORGANISM: Homo Sapiens

<400> SEQUENCE: 25

Leu Leu Gly Ile Lys Arg Leu Arg Leu Tyr Cys Asn Val Gly Ile
1               5                   10                  15

Gly Phe His Leu Gln Ala Leu Pro Asp Gly Arg Ile Gly Gly Ala His
            20                  25                  30

Ala Asp Thr Arg Asp Ser Leu Leu Glu Leu Ser Pro Val Glu Arg Gly
        35                  40                  45

Val Val Ser Ile Phe Gly Val Ala Ser Arg Phe Phe Val Ala Met Ser
    50                  55                  60

Ser Lys Gly Lys Leu Tyr Gly Ser Pro Phe Phe Thr Asp Glu Cys Thr
65                  70                  75                  80

Phe Lys Glu Ile Leu Leu Pro Asn Asn Tyr Asn Ala Tyr Glu Ser Tyr
                85                  90                  95

Lys Tyr Pro Gly Met Phe Ile Ala Leu Ser Lys Asn Gly Lys Thr Lys
            100                 105                 110

Lys Gly Asn Arg Val Ser Pro Thr Met Lys Val Thr His Phe Leu Pro
        115                 120                 125

Arg Leu
    130

<210> SEQ ID NO 26
<211> LENGTH: 130
<212> TYPE: PRT
<213> ORGANISM: Homo Sapiens

<400> SEQUENCE: 26

Leu Val Gly Ile Lys Arg Gln Arg Arg Leu Tyr Cys Asn Val Gly Ile
1               5                   10                  15

Gly Phe His Leu Gln Val Leu Pro Asp Gly Arg Ile Ser Gly Thr His
            20                  25                  30

Glu Glu Asn Pro Tyr Ser Leu Leu Glu Ile Ser Thr Val Glu Arg Gly
        35                  40                  45

Val Val Ser Leu Phe Gly Val Arg Ser Ala Leu Phe Val Ala Met Asn
    50                  55                  60

Ser Lys Gly Arg Leu Tyr Ala Thr Pro Ser Phe Gln Glu Glu Cys Lys
65                  70                  75                  80

Phe Arg Glu Thr Leu Leu Pro Asn Asn Tyr Asn Ala Tyr Glu Ser Asp
                85                  90                  95

Leu Tyr Gln Gly Thr Tyr Ile Ala Leu Ser Lys Tyr Gly Arg Val Lys
            100                 105                 110
```

Arg Gly Ser Lys Val Ser Pro Ile Met Thr Val Thr His Phe Leu Pro
            115                 120                 125

Arg Ile
    130

<210> SEQ ID NO 27
<211> LENGTH: 144
<212> TYPE: PRT
<213> ORGANISM: Homo Sapiens

<400> SEQUENCE: 27

Ser Pro Ser Gly Arg Arg Thr Gly Ser Leu Tyr Cys Arg Val Gly Ile
1               5                   10                  15

Gly Phe His Leu Gln Ile Tyr Pro Asp Gly Lys Val Asn Gly Ser His
            20                  25                  30

Glu Ala Asn Met Leu Ser Val Leu Glu Ile Phe Ala Val Ser Gln Gly
        35                  40                  45

Ile Val Gly Ile Arg Gly Val Phe Ser Asn Lys Phe Leu Ala Met Ser
    50                  55                  60

Lys Lys Gly Lys Leu His Ala Ser Ala Lys Phe Thr Asp Asp Cys Lys
65                  70                  75                  80

Phe Arg Glu Arg Phe Gln Glu Asn Ser Tyr Asn Thr Tyr Ala Ser Ala
                85                  90                  95

Ile His Arg Thr Glu Lys Thr Gly Arg Glu Trp Tyr Val Ala Leu Asn
            100                 105                 110

Lys Arg Gly Lys Ala Lys Arg Gly Cys Ser Pro Arg Val Lys Pro Gln
        115                 120                 125

His Ile Ser Thr His Phe Leu Pro Arg Phe Lys Gln Ser Glu Gln Pro
    130                 135                 140

<210> SEQ ID NO 28
<211> LENGTH: 137
<212> TYPE: PRT
<213> ORGANISM: Homo Sapiens

<400> SEQUENCE: 28

Val Ser Arg Lys Gln Leu Arg Leu Tyr Gln Leu Tyr Ser Arg Thr Ser
1               5                   10                  15

Gln Lys His Ile Gln Val Leu Gly Arg Arg Ile Ser Ala Arg Gly Glu
            20                  25                  30

Asp Gly Asp Lys Tyr Ala Gln Leu Leu Val Glu Thr Asp Thr Phe Gly
        35                  40                  45

Ser Gln Val Arg Ile Lys Gly Lys Glu Thr Lys Phe Tyr Leu Cys Met
    50                  55                  60

Asn Arg Lys Gly Lys Leu Val Gly Lys Pro Asp Gly Thr Ser Lys Glu
65                  70                  75                  80

Cys Val Phe Ile Glu Lys Val Leu Glu Asn Asn Tyr Thr Ala Leu Met
                85                  90                  95

Ser Ala Lys Tyr Ser Gly Trp Tyr Val Gly Phe Thr Lys Lys Gly Arg
            100                 105                 110

Pro Arg Lys Gly Pro Lys Thr Arg Glu Asn Gln Gln Asp Val His Phe
        115                 120                 125

Met Lys Arg Tyr Pro Lys Gly Gln Pro
    130                 135

-continued

```
<210> SEQ ID NO 29
<211> LENGTH: 139
<212> TYPE: PRT
<213> ORGANISM: Homo Sapiens

<400> SEQUENCE: 29

Leu Ser Arg Arg Leu Ile Arg Thr Tyr Gln Leu Tyr Ser Arg Thr Ser
1               5                   10                  15

Gly Lys His Val Gln Val Leu Ala Asn Lys Arg Ile Asn Ala Met Ala
            20                  25                  30

Glu Asp Gly Thr Pro Phe Ala Lys Leu Ile Val Glu Thr Asp Thr Lys
        35                  40                  45

Gly Ser Arg Val Arg Val Arg Gly Ala Glu Thr Gly Leu Tyr Ile Cys
    50                  55                  60

Met Asn Lys Lys Gly Lys Leu Ile Ala Lys Ser Asn Gly Lys Gly Lys
65                  70                  75                  80

Asp Cys Val Phe Thr Phe Ile Val Leu Glu Asn Asn Tyr Thr Ala Leu
                85                  90                  95

Gln Asn Ala Lys Tyr Gly Glu Trp Tyr Met Asn Phe Thr Arg Lys Gly
            100                 105                 110

Arg Pro Arg Lys Gly Ser Lys Thr Arg Gln His Gln Arg Glu Val His
        115                 120                 125

Phe Met Lys Arg Leu Pro Arg Gly His His Thr
    130                 135

<210> SEQ ID NO 30
<211> LENGTH: 138
<212> TYPE: PRT
<213> ORGANISM: Homo Sapiens

<400> SEQUENCE: 30

Leu Ser Arg Arg Gln Ile Arg Glu Tyr Gln Leu Tyr Ser Arg Thr Ser
1               5                   10                  15

Gly Lys His Val Gln Val Thr Gly Arg Arg Ile Ser Ala Thr Ala Glu
            20                  25                  30

Asp Gly Asn Lys Phe Lys Lys Leu Ile Val Glu Thr Asp Thr Phe Gly
        35                  40                  45

Ser Arg Val Arg Ile Lys Gly Ala Glu Ser Glu Lys Tyr Ile Cys Met
    50                  55                  60

Asn Lys Arg Gly Lys Leu Ile Gly Lys Pro Ser Gly Lys Ser Lys Asp
65                  70                  75                  80

Cys Val Phe Thr Glu Ile Val Leu Glu Asn Asn Tyr Thr Ala Phe Gln
                85                  90                  95

Asn Ala Arg His Glu Gly Trp Phe Met Ala Phe Thr Arg Gln Gly Arg
            100                 105                 110

Pro Arg Gln Ala Ser Arg Ser Arg Gln Asn Gln Arg Glu Ala His Phe
        115                 120                 125

Ile Lys Arg Leu Tyr Gln Gly Gln Leu Pro
    130                 135

<210> SEQ ID NO 31
<211> LENGTH: 135
<212> TYPE: PRT
<213> ORGANISM: Homo Sapiens
```

-continued

```
<400> SEQUENCE: 31

Gly Trp Gly Lys Ile Thr Arg Leu Gln Tyr Leu Tyr Ser Ala Gly Pro
1               5                   10                  15

Tyr Val Ser Asn Cys Phe Leu Arg Ile Arg Ser Asp Gly Ser Val Asp
            20                  25                  30

Cys Glu Glu Asp Gln Asn Glu Arg Asn Leu Leu Glu Phe Arg Ala Val
        35                  40                  45

Ala Leu Lys Thr Ile Ala Ile Lys Asp Val Ser Ser Val Arg Tyr Leu
    50                  55                  60

Cys Met Ser Ala Asp Gly Lys Ile Tyr Gly Leu Ile Arg Tyr Ser Glu
65                  70                  75                  80

Glu Asp Cys Thr Phe Arg Glu Glu Met Asp Cys Leu Gly Tyr Asn Gln
                85                  90                  95

Tyr Arg Ser Met Lys His His Leu His Ile Ile Phe Ile Gln Ala Lys
            100                 105                 110

Pro Arg Glu Gln Leu Gln Asp Gln Lys Pro Ser Asn Phe Ile Pro Val
        115                 120                 125

Phe His Arg Ser Phe Phe Glu
    130                 135

<210> SEQ ID NO 32
<211> LENGTH: 139
<212> TYPE: PRT
<213> ORGANISM: Homo Sapiens

<400> SEQUENCE: 32

Gly Trp Gly Asp Pro Ile Arg Leu Arg His Leu Tyr Thr Ser Gly Pro
1               5                   10                  15

His Gly Leu Ser Ser Cys Phe Leu Arg Ile Arg Ala Asp Gly Val Val
            20                  25                  30

Asp Cys Ala Arg Gly Gln Ser Ala His Ser Leu Leu Glu Ile Lys Ala
        35                  40                  45

Val Ala Leu Arg Thr Val Ala Ile Lys Gly Val His Ser Val Arg Tyr
    50                  55                  60

Leu Cys Asn Gly Ala Asp Gly Lys Asn Gln Gly Leu Leu Gln Tyr Ser
65                  70                  75                  80

Glu Glu Asp Cys Ala Phe Glu Glu Glu Ile Arg Pro Asp Gly Tyr Asn
                85                  90                  95

Val Tyr Arg Ser Glu Lys His Arg Leu Pro Val Ser Leu Ser Ser Ala
            100                 105                 110

Lys Gln Arg Gln Leu Tyr Lys Asn Arg Gly Phe Leu Pro Leu Ser His
        115                 120                 125

Phe Leu Pro Met Leu Pro Met Val Pro Glu Glu
    130                 135

<210> SEQ ID NO 33
<211> LENGTH: 136
<212> TYPE: PRT
<213> ORGANISM: Homo Sapiens

<400> SEQUENCE: 33

Gln Phe Gly Gly Gln Val Arg Gln Arg Tyr Leu Tyr Thr Asp Asp Ala
1               5                   10                  15

Gln Gln Thr Glu Ala His Leu Glu Ile Arg Glu Asp Gly Thr Val Gly
            20                  25                  30
```

```
Gly Ala Ala Asp Gln Ser Pro Glu Ser Leu Leu Gln Leu Lys Ala Leu
             35                  40                  45

Lys Pro Gly Val Ile Gln Ile Leu Gly Val Lys Thr Ser Arg Phe Leu
 50                  55                  60

Cys Gln Arg Glu Asp Gly Ala Leu Tyr Gly Ser Leu His Phe Asp Pro
 65                  70                  75                  80

Glu Ala Cys Ser Phe Arg Glu Leu Leu Leu Glu Asp Gly Tyr Asn Val
                 85                  90                  95

Tyr Gln Ser Glu Ala His Gly Leu Pro Leu His Leu Pro Gly Asn Lys
                100                 105                 110

Ser Pro His Arg Asp Pro Ala Pro Arg Gly Pro Ala Arg Phe Leu Pro
            115                 120                 125

Leu Pro Gly Leu Pro Pro Ala Leu
    130                 135

<210> SEQ ID NO 34
<211> LENGTH: 145
<212> TYPE: PRT
<213> ORGANISM: Homo Sapiens

<400> SEQUENCE: 34

Ser Trp Gly Gly Leu Ile His Leu Tyr Thr Ala Thr Ala Arg Asn Ser
 1               5                  10                  15

Tyr His Leu Gln Ile His Lys Asn Gly His Val Asp Gly Ala Pro His
                 20                  25                  30

Gly Thr Ile Tyr Ser Ala Leu Met Ile Arg Ser Glu Asp Ala Gly Phe
             35                  40                  45

Val Val Ile Thr Gly Val Met Ser Arg Arg Tyr Leu Cys Met Asp Phe
 50                  55                  60

Arg Gly Asn Ile Phe Gly Ser His Tyr Phe Asp Pro Glu Asn Cys Arg
 65                  70                  75                  80

Phe Gln His Gln Thr Leu Glu Asn Gly Tyr Asp Val Tyr His Ser Pro
                 85                  90                  95

Gln Tyr His Phe Leu Val Ser Leu Gly Arg Ala Lys Arg Ala Phe Leu
                100                 105                 110

Pro Gly Met Asn Pro Pro Pro Tyr Ser Gln Phe Leu Ser Arg Arg Asn
            115                 120                 125

Glu Ile Pro Leu Ile His Phe Asn Thr Pro Ile Pro Arg Arg His Thr
130                 135                 140

Arg
145

<210> SEQ ID NO 35
<211> LENGTH: 4
<212> TYPE: PRT
<213> ORGANISM: Unknown
<220> FEATURE:
<221> NAME/KEY: Variant
<222> LOCATION: (2)..(3)
<223> OTHER INFORMATION: Xaa can be any naturally occurring amino
      acid
<220> FEATURE:
<221> NAME/KEY: Variant
<222> LOCATION: (4)..(4)
<223> OTHER INFORMATION: Xaa = R or S

<400> SEQUENCE: 35

Arg Xaa Xaa Xaa
 1
```